United States Patent
Hiroshima et al.

(10) Patent No.: US 11,076,827 B2
(45) Date of Patent: Aug. 3, 2021

(54) ULTRASOUND IMAGE CAPTURING DEVICE AND METHOD OF PROCESSING ULTRASOUND SIGNAL

(71) Applicant: Hitachi, Ltd., Tokyo (JP)

(72) Inventors: Misaki Hiroshima, Tokyo (JP); Teiichiro Ikeda, Tokyo (JP); Chizue Ishihara, Tokyo (JP)

(73) Assignee: HITACHI, LTD., Tokyo (JP)

( * ) Notice: Subject to any disclaimer, the term of this patent is extended or adjusted under 35 U.S.C. 154(b) by 983 days.

(21) Appl. No.: 15/550,099

(22) PCT Filed: Feb. 4, 2016

(86) PCT No.: PCT/JP2016/053396
§ 371 (c)(1),
(2) Date: Aug. 10, 2017

(87) PCT Pub. No.: WO2016/132924
PCT Pub. Date: Aug. 25, 2016

(65) Prior Publication Data
US 2018/0021012 A1    Jan. 25, 2018

(30) Foreign Application Priority Data
Feb. 18, 2015    (JP) .............................. JP2015-030016

(51) Int. Cl.
*A61B 8/14*    (2006.01)
*A61B 8/00*    (2006.01)
*G01S 15/89*    (2006.01)

(52) U.S. Cl.
CPC .............. *A61B 8/14* (2013.01); *A61B 8/4488* (2013.01); *G01S 15/8925* (2013.01)

(58) Field of Classification Search
None
See application file for complete search history.

(56) References Cited

U.S. PATENT DOCUMENTS

| 5,623,928 A | 4/1997 | Wright et al. |
| 5,667,373 A | 9/1997 | Wright et al. |

(Continued)

FOREIGN PATENT DOCUMENTS

| CN | 102138807 A | 8/2011 |
| JP | 2004-261229 A | 9/2004 |
| JP | 2006187667 A | 7/2006 |
| JP | 2011-45708 A | 3/2011 |

(Continued)

OTHER PUBLICATIONS

International Preliminary Report on Patentability received in corresponding International Application No. PCT/JP2016/053396 dated Aug. 31, 2017.

(Continued)

*Primary Examiner* — Pascal M Bui Pho
*Assistant Examiner* — Marjan Saboktakin
(74) *Attorney, Agent, or Firm* — Mattingly & Malur, PC

(57) ABSTRACT

Without using any approximated wave front propagation model, appropriate delay times are set for received signals to obtain phased signals for both the inside and outside of irradiation area of transmission beam.
A reception beamformer comprises a wave front propagation calculator 121 that obtains times until ultrasonic waves transmitted from a plurality of ultrasonic transducers arrive at a reception focus by calculation, and a delay time extractor 122 that calculates delay times for the reception focus on the basis of distribution of the arrival times of the ultrasonic waves for each of the plurality of the ultrasonic transducers obtained by the wave front propagation calculator 121. Therefore, even if the wave front that arrives at the reception focus has a complicated shape, it is not necessary to approximate the wave front, and phasing addition can be performed with appropriate delay times obtained from times until the ultrasonic waves arrive at the reception focus.

6 Claims, 22 Drawing Sheets

(56) References Cited

U.S. PATENT DOCUMENTS

Figure 2:
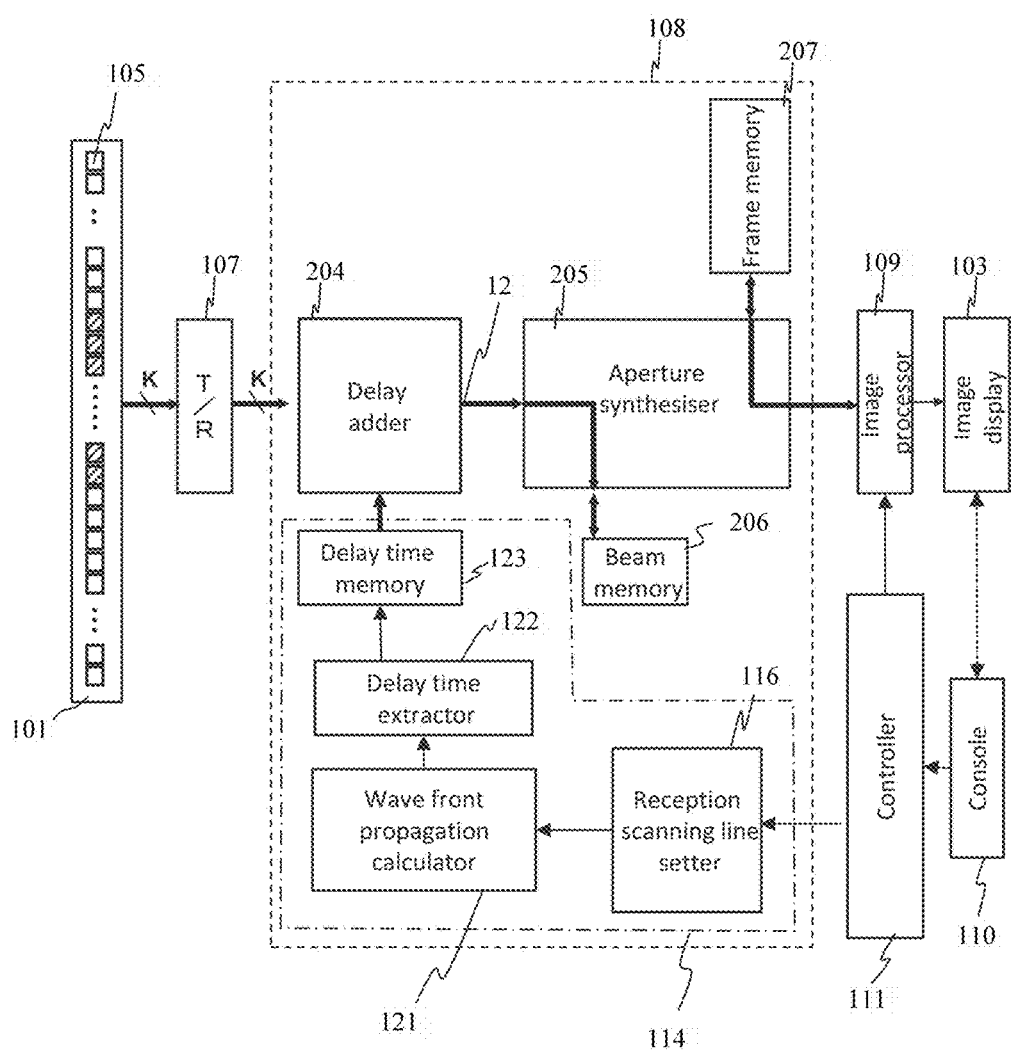

| | | |
|---|---|---|
| 5,685,308 A | 11/1997 | Wright et al. |
| 5,793,701 A | 8/1998 | Wright et al. |
| 5,827,188 A | 10/1998 | Wright et al. |
| 5,882,307 A | 3/1999 | Wright et al. |
| 5,921,932 A | 7/1999 | Wright et al. |
| 5,928,152 A | 7/1999 | Wright et al. |
| 6,016,285 A | 1/2000 | Wright et al. |
| 6,029,116 A | 2/2000 | Wright et al. |
| 6,231,511 B1 | 5/2001 | Bae |
| 2006/0241444 A1 | 10/2006 | Nishigaki |
| 2012/0078105 A1 | 3/2012 | Kamiyama |
| 2015/0025385 A1 | 1/2015 | Ikeda et al. |
| 2015/0351720 A1 | 12/2015 | Ikeda et al. |
| 2016/0120503 A1* | 5/2016 | Tsushima ............. A61B 8/5207 367/7 |
| 2016/0367224 A1* | 12/2016 | Yamamoto ............... A61B 8/14 |

FOREIGN PATENT DOCUMENTS

| | | |
|---|---|---|
| JP | 2011045708 A | 3/2011 |
| WO | 01/26555 A1 | 4/2001 |
| WO | 2013/121842 A1 | 8/2013 |
| WO | 2013121842 A1 | 8/2013 |
| WO | 2014/109392 A1 | 7/2014 |
| WO | 2014109392 A1 | 7/2014 |

OTHER PUBLICATIONS

Chinese Office Action received in corresponding Chinese Application No. 201680009160.X dated Jul. 15, 2019.
International Search Report of PCT/JP2016/053396 dated Mar. 8, 2016.
Extended European Search Report received in corresponding European Application No. 16752311.7 dated Aug. 24, 2018.

* cited by examiner

Fig. 1
(a)
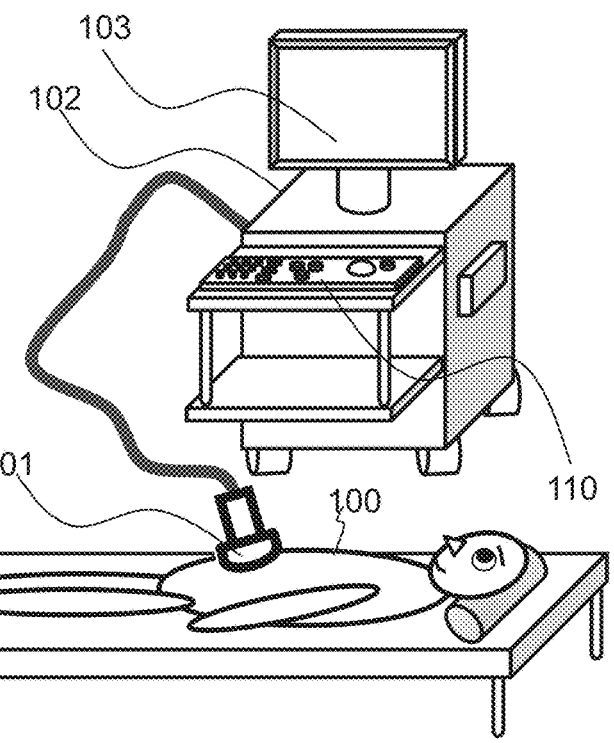
(b)
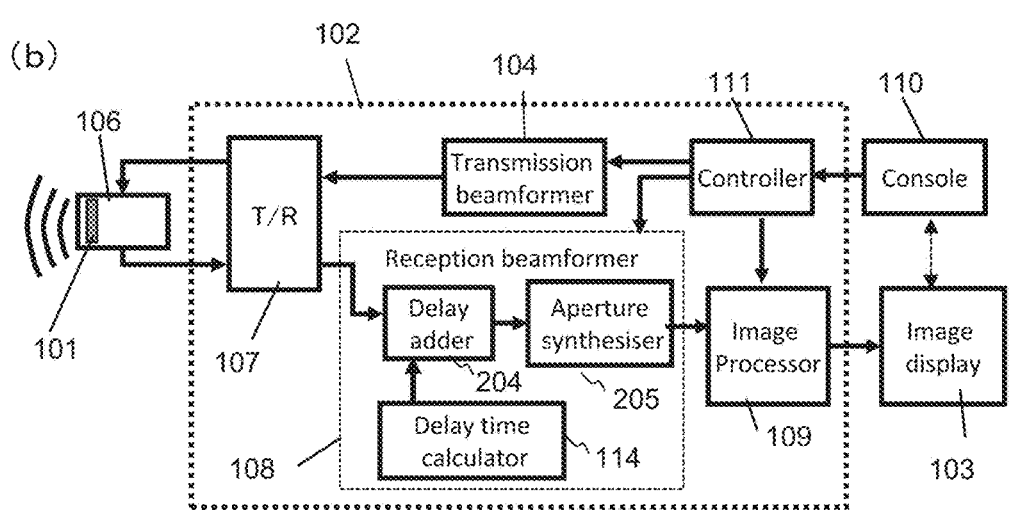

(a)                          (b)

ULTRASOUND IMAGE CAPTURING DEVICE AND METHOD OF PROCESSING ULTRASOUND SIGNAL

TECHNICAL FIELD

The present invention relates to an ultrasonic imaging technique for obtaining an image of the inside of a subject using an ultrasonic wave.

BACKGROUND ART

Ultrasonic imaging technique is a technique for non-invasively imaging the inside of a subject such as human body using an ultrasonic wave (inaudible sound wave, generally a sound wave of such a high frequency as 20 kHz or higher).

There are two kinds of methods of transmitting ultrasonic beams from a plurality of ultrasonic transducers of an ultrasound probe to a subject, i.e., expansion transmission in which ultrasonic beams spreading in a fan shape are transmitted, and convergence transmission in which ultrasonic beams are transmitted so as to converge at a transmission focus set in the inside of a subject.

Ultrasonic waves reflected in a subject are received by a plurality of ultrasonic transducers of an ultrasound probe, and a plurality of received signals are delayed by a delay time set for every ultrasonic transducer depending on reception focus (phasing), and then added. The delay time for the phasing is determined with an approximated curve (delay curve) based on a wave front propagation model of a transmission beam.

Patent document 1 discloses an aperture synthesis method for performing convergence transmission with a single focus. The delay calculation disclosed in Patent document 1 uses a virtual sound source method, in which the delay time is set for every ultrasonic transducer depending on reception focus by using a wave front propagation model based on the assumption that a spherical wave is transmitted from a transmission focus. The received signals received by a plurality of the ultrasonic transducers are each delayed by delay times set by the virtual sound source method, focused on the reception focus, and then added to obtain phased signals. By synthesizing and thereby superimposing these phased signals and phased signals acquired in one or more times of other transmission and reception for the same reception focus, aperture synthesis is performed.

By the aperture synthesis, phased signals obtained for a certain point by transmissions and receptions performed in different directions with an ultrasound probe can be superimposed, therefore, for example, higher resolution of point image can be provided, and robustness against heterogeneity can be imparted. Furthermore, since the processing gain is improved by the superimposition processing, the number of transmission of ultrasonic waves can be reduced compared with that of usual cases, and therefore it can also be applied to high-speed imaging.

Patent document 2 discloses a technique of detecting phase shifts of received signals obtained by a plurality of times of different transmissions resulting from body motions of a subject, heterogeneity of acoustic velocity in a subject, and so forth, and performing the aperture synthesis after coinciding the phases. With this technique, the processing gain can be improved by superimposing phased signals by the aperture synthesis even for received signals for the same reception focus obtained by different transmissions and receptions and having different phases.

Patent document 3 discloses a technique for generating phased signals even under the conditions that there are body motions by memorizing a plurality of delay time data sets geometrically obtained beforehand, and adjusting the reception focus by extending the values of the data sets by real-time calculation.

PRIOR ART REFERENCES

Patent Documents

Patent document 1: U.S. Pat. No. 6,231,511
Patent document 2: Japanese Patent Unexamined Publication (KOKAI) No. 2004-261229
Patent document 3: Japanese Patent Unexamined Publication (KOKAI) No. 2006-187667

SUMMARY OF THE INVENTION

Object to be Achieved by the Invention

In the techniques of Patent documents 1 to 3, wave fronts are approximated on the bases of a wave front propagation model defined beforehand such as those defined by the virtual sound source method, and delay times are calculated from the approximated wave fronts. However, when non-spherical focusing is performed, or when a transmission beam, especially a transmission beam having a plurality of transmission focuses, is transmitted by using a ultrasound probe comprising a 2D array having ultrasonic transducers two-dimensionally arranged thereon, the wave front of the transmitted ultrasonic beam has a complicated shape, and if a known wave front propagation model is applied to such a wave front, difference of the actual wave front and the approximated wave front becomes significant. Therefore, it becomes difficult to obtain phased signals reflecting the structure of the subject.

Even if an ultrasound probe having ultrasonic transducers one dimensionally arranged thereon is used, the region for which phasing can be performed by applying a virtual sound source wave front model is limited to the inside of a region where the transmission beam is directly irradiated (geometrical region in the shape of sandglass formed by connecting both ends of the apertures of the ultrasound probe and focus). Out of the geometrical region of the transmission beam, the shape of the wave front becomes complicated, and modeling of the wave front is difficult. For this reason, for a region out of the region where the transmission beam is directly irradiated, phased signals cannot be obtained, and the aperture synthesis cannot be performed, either.

An object of the present invention is to obtain phased signals for both the inside and outside of the region where the transmission beam is directly irradiated by setting appropriate delay times for received signals obtained in the regions without using any approximated wave front propagation model.

Means for Achieving the Object

The present invention provides an ultrasonic imaging apparatus comprising a transmission beamformer that transmits, from a plurality of arranged ultrasonic transducers, ultrasonic waves delayed for each of the plurality of the ultrasonic transducers so that a predetermined transmission beam is formed, and a reception beamformer that delays received signals outputted by the plurality of the ultrasonic transducers after receiving the ultrasonic waves for a predetermined reception focus by delay times set for each of the plurality of the ultrasonic transducers, and then adds the signals to obtain phased signals. The reception beamformer comprises a delay time calculator that obtains the delay times by calculation. The delay time calculator comprises a wave front propagation calculator that obtains times until each of the ultrasonic waves transmitted from the plurality of the ultrasonic transducers arrives at the reception focus by calculation, and a delay time extractor that calculates the delay times for the reception focus on the basis of distribution of the arrival times of the ultrasonic waves for the plurality of the ultrasonic transducers obtained by the wave front propagation calculator.

Effect of the Invention

According to the present invention, phased signals can be obtained for both the inside and outside of a irradiation region of transmission beam by setting appropriate delay times for received signals without using any approximated wave front propagation model, and therefore delay calculation adapted to an actual wave front can be performed even in transmission beamforming in which the wave front shape becomes complicated.

BRIEF DESCRIPTIONS OF THE DRAWINGS

[FIG. 1] FIG. 1A: A perspective view of the ultrasonic imaging apparatus of the first embodiment, FIG. 1B: a block diagram of the same.

[FIG. 2] A block diagram showing the configuration of the reception beamformer according to the first embodiment.

Figure 3:
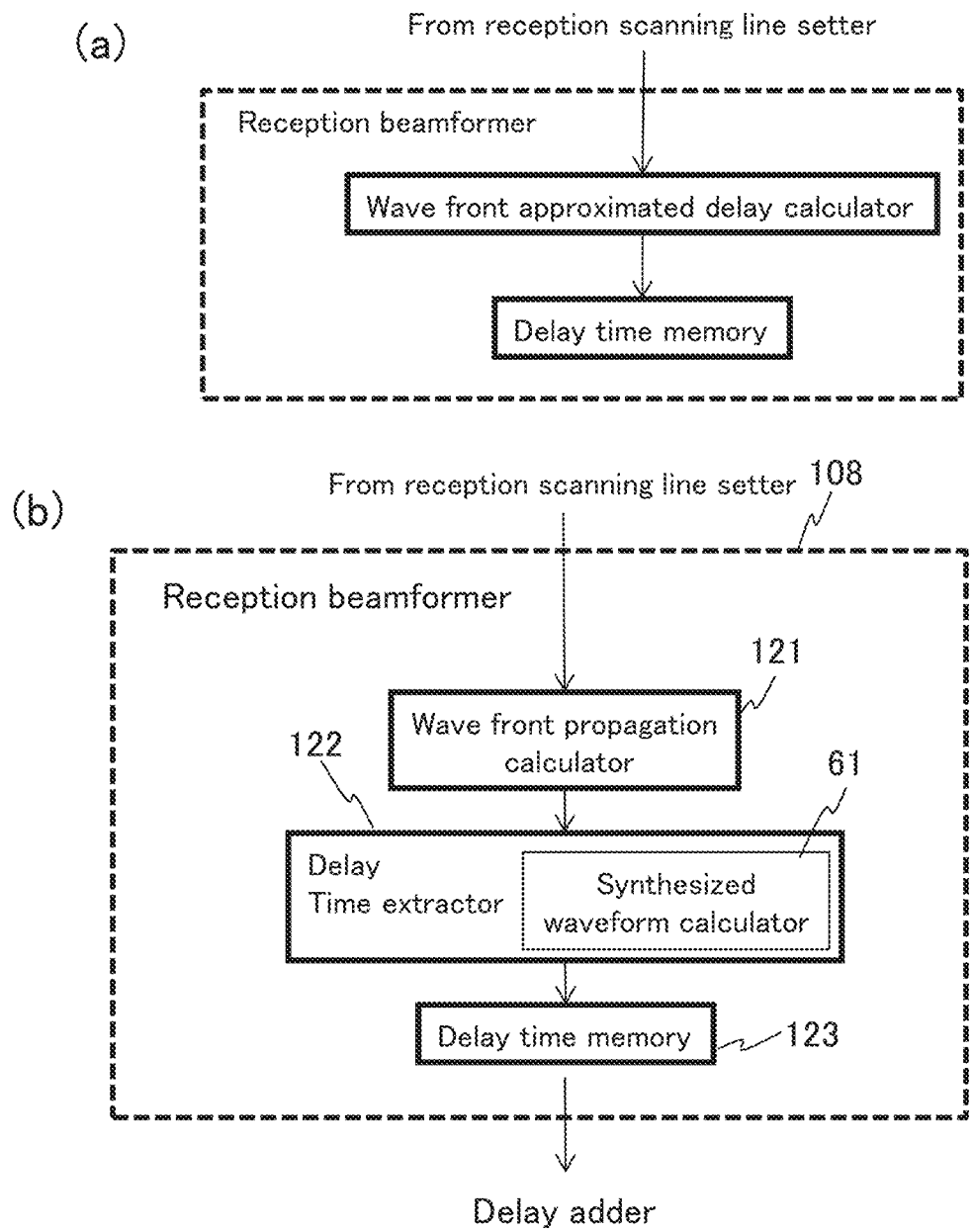

[FIG. 3] FIG. 3A: A block diagram showing a configuration of a conventional reception beamformer, FIG. 3B: a block diagram showing the configuration of the reception beamformer according to the first embodiment.

Figure 4:
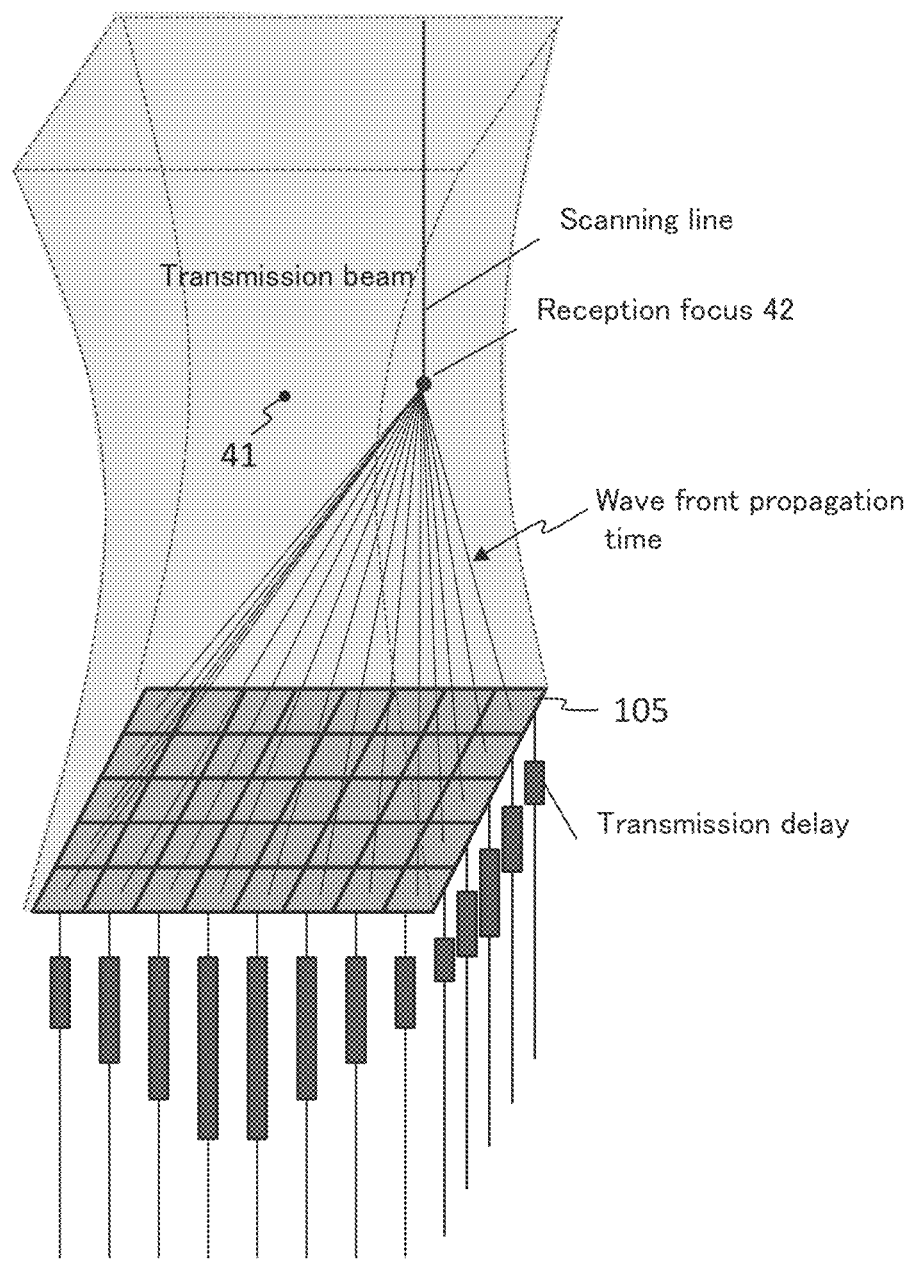

[FIG. 4] An explanatory drawing showing time until ultrasonic waves transmitted from ultrasonic transducers arrive at the reception focus 42.

Figure 5:
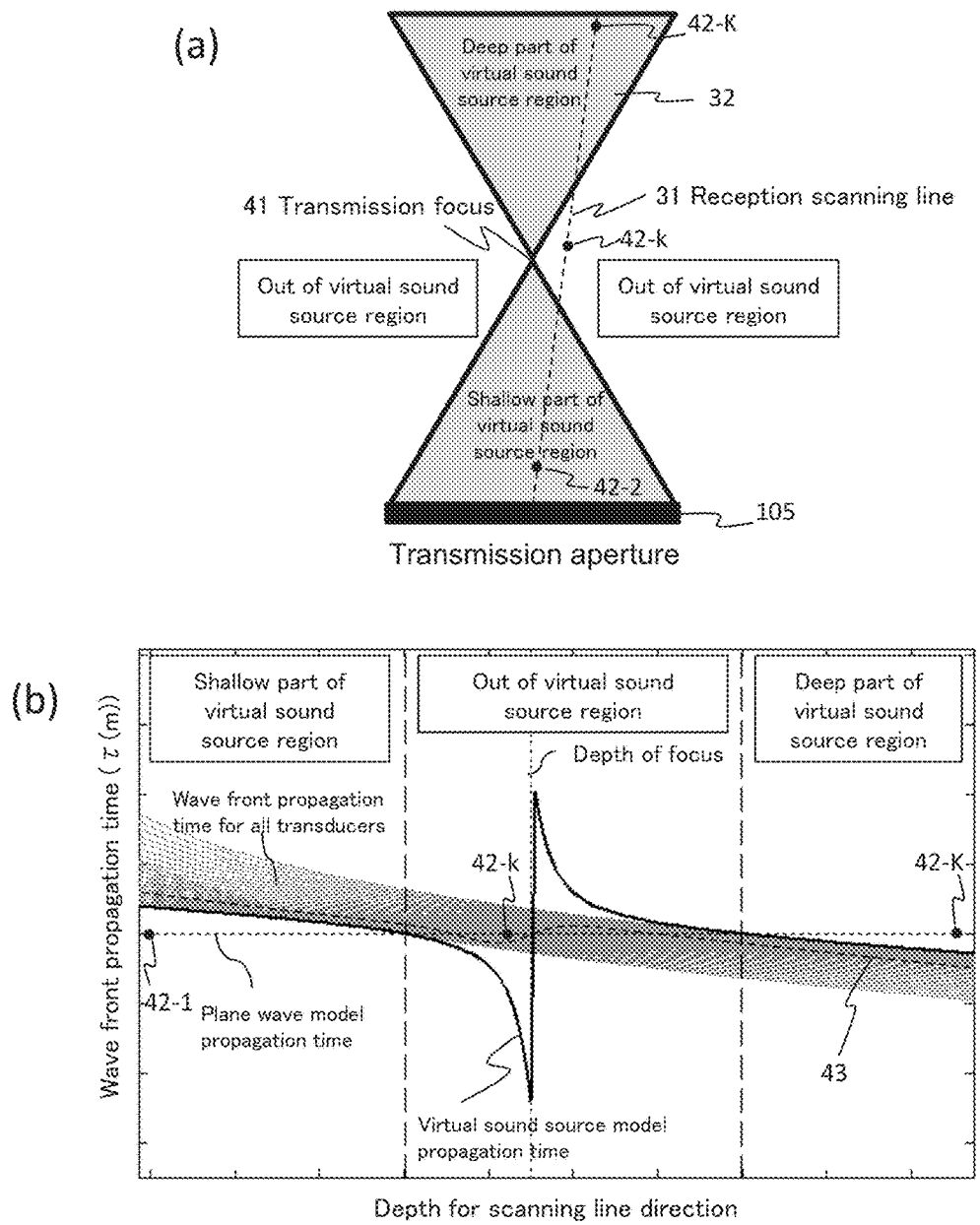

[FIG. 5] FIG. 5A: An explanatory drawing showing a direct irradiation area of the transmission beam 32 and reception scanning lines of the ultrasonic imaging apparatus according to the first embodiment, FIG. 5B: a graph exemplifying curves of wave front propagation times for all the transmission transducers of the same.

Figure 6:
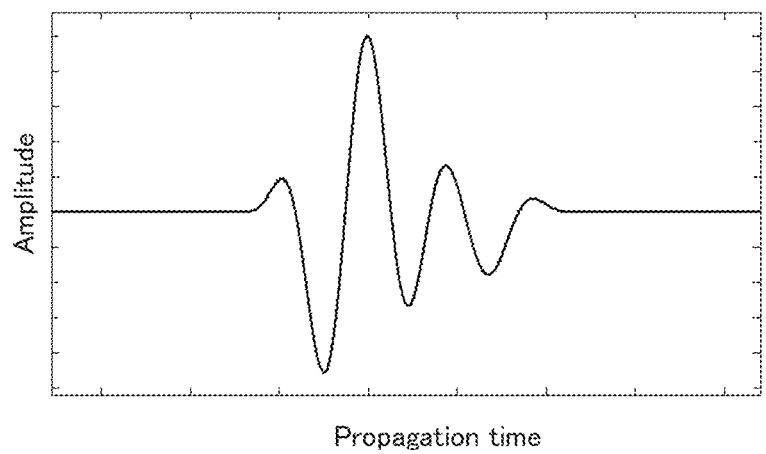

[FIG. 6] An explanatory drawing showing a synthesized waveform of ultrasonic waves that arrive at a certain reception focus according to the first embodiment.

Figure 7:
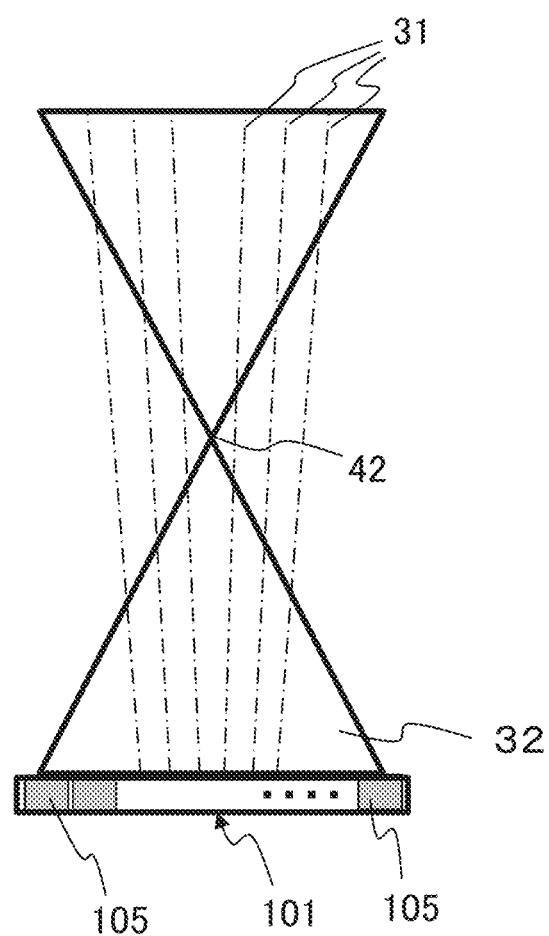

[FIG. 7] An explanatory drawing showing a direct irradiation area of the transmission beam 32, and a plurality of reception scanning lines.

Figure 8:
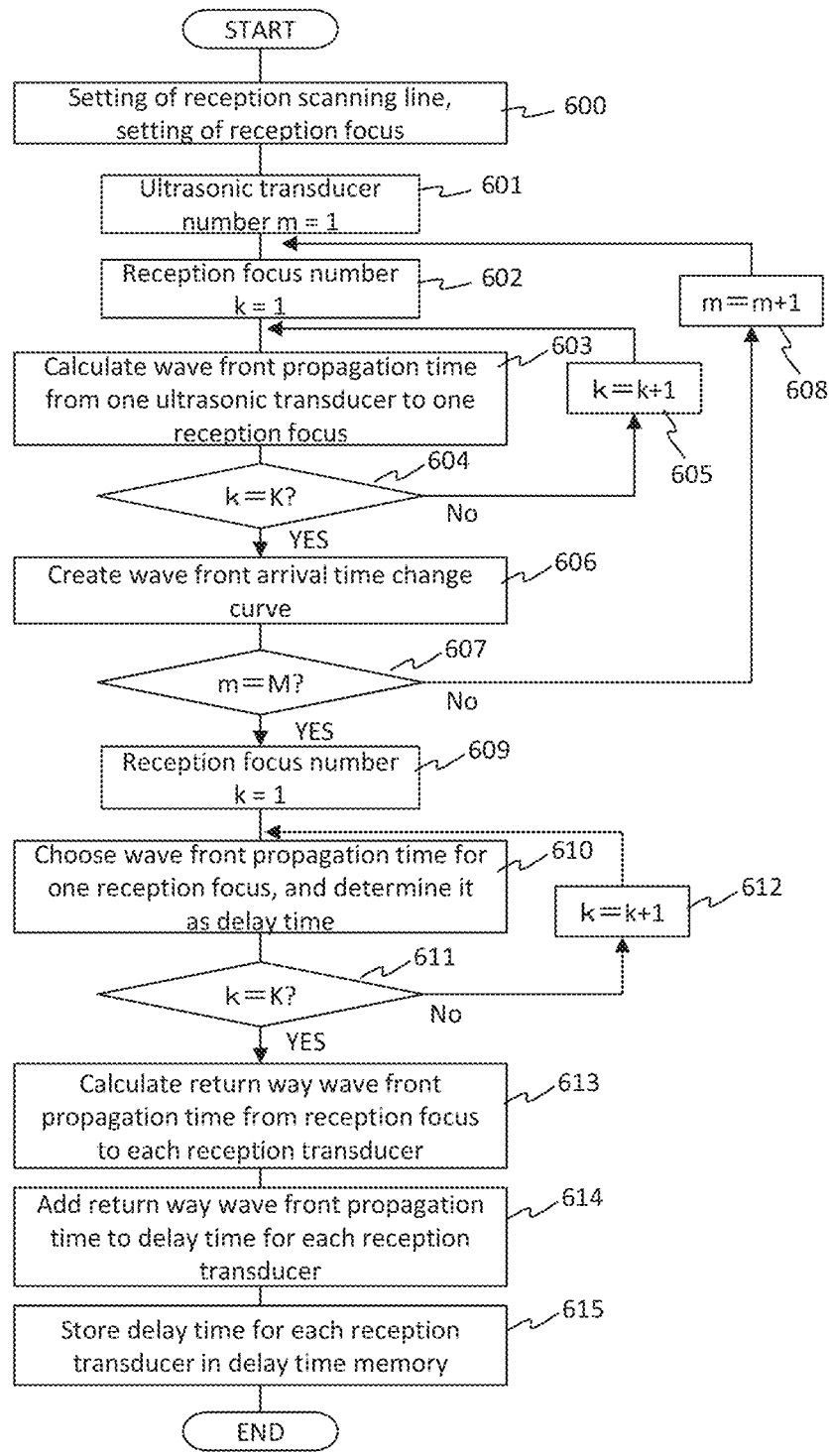

[FIG. 8] A flowchart showing operations of the delay time calculator according to the first embodiment.

Figure 9:
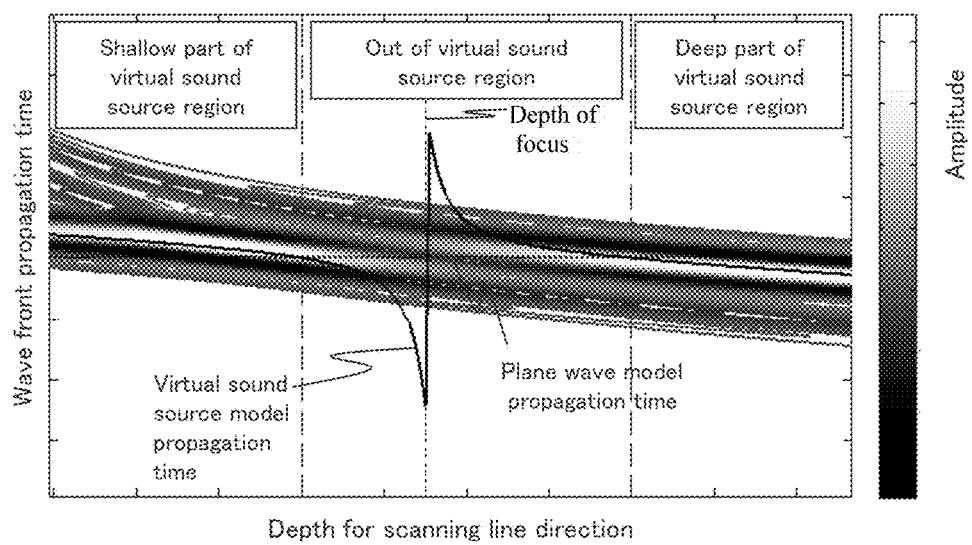

[FIG. 9] An explanatory drawing that exemplifies distribution of amplitude values of the synthesized waveforms of the ultrasonic waves on the scanning lines according to the first embodiment.

Figure 10:
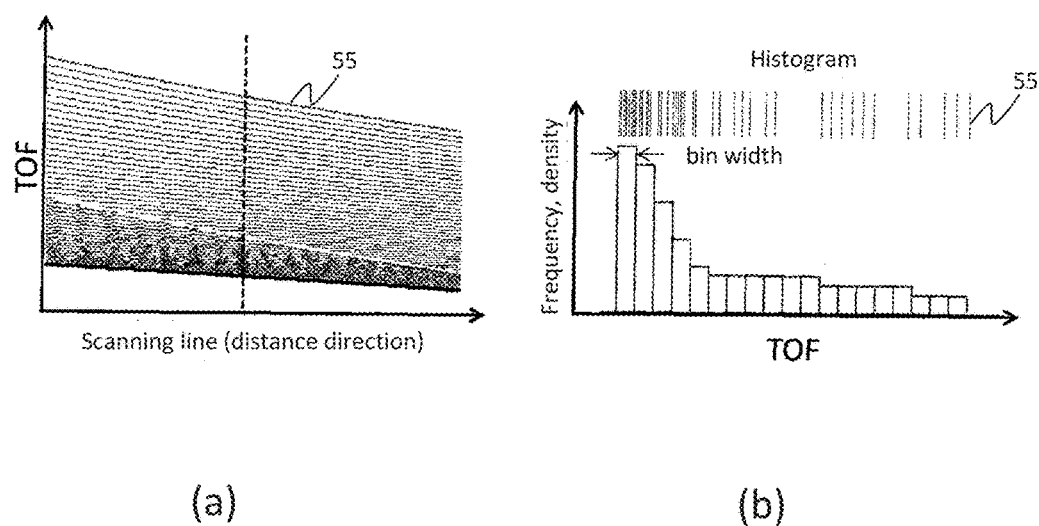

[FIG. 10] FIG. 10A: A graph that exemplifies curves of the wave front propagation times for all the transmission transducers, FIG. 10B: a histogram that shows frequency of the wave front propagation times.

Figure 11:
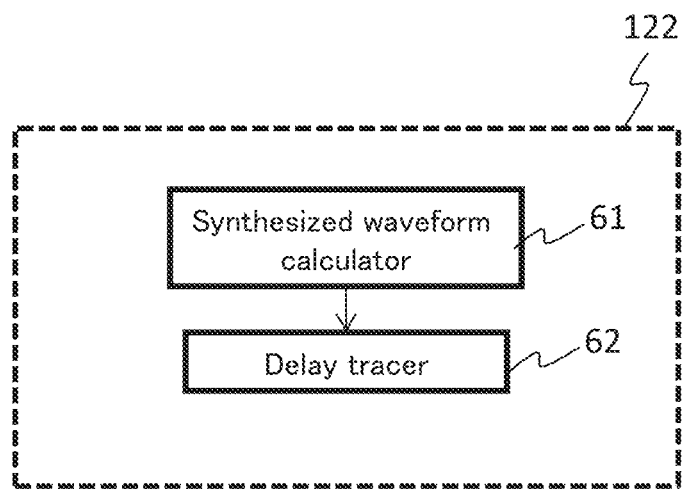

[FIG. 11] A block diagram of the delay time extractor 122 according to the third embodiment.

Figure 12:
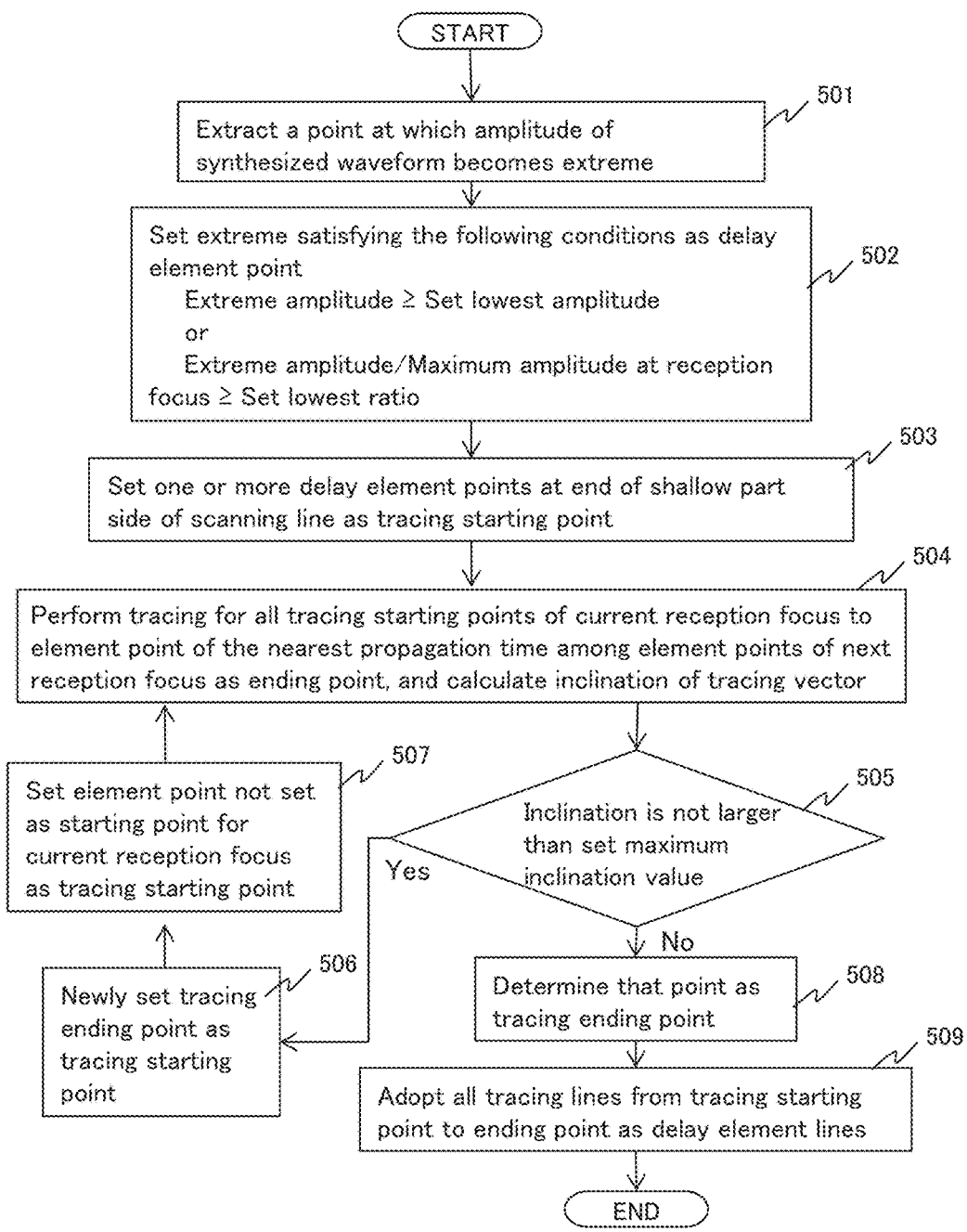

[FIG. 12] A flowchart showing operations of the delay tracer according to the third embodiment.

Figure 13:
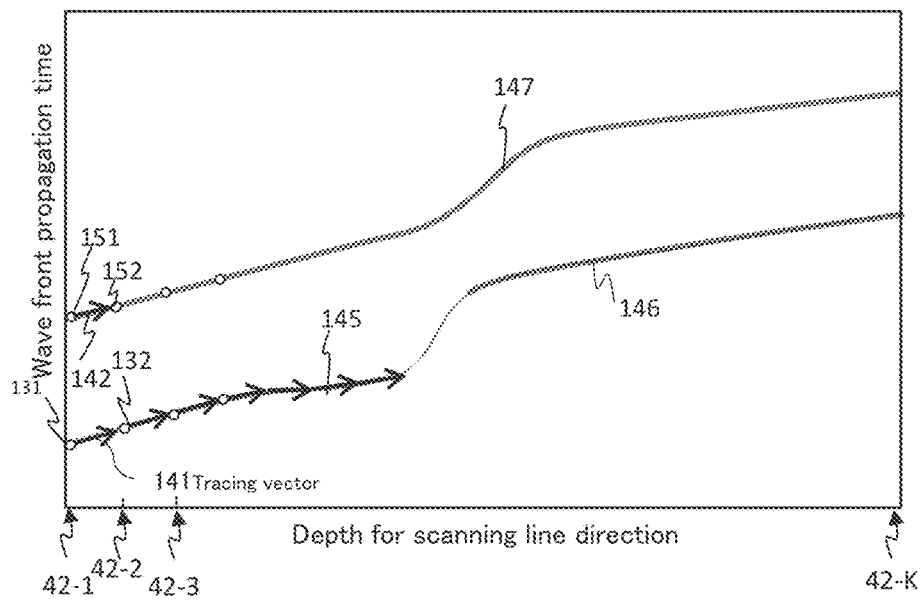

[FIG. 13] An explanatory drawing showing traced delay element lines.

Figure 14:
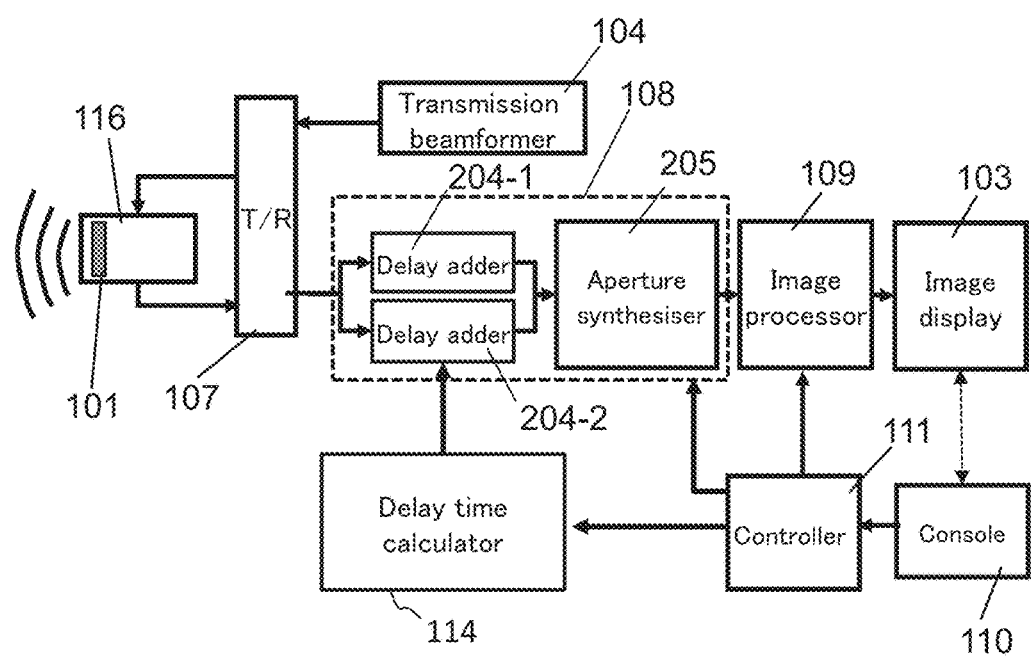

[FIG. 14] A block diagram of the ultrasonic imaging apparatus comprising a plurality of delay adders according to the third embodiment.

Figure 15:
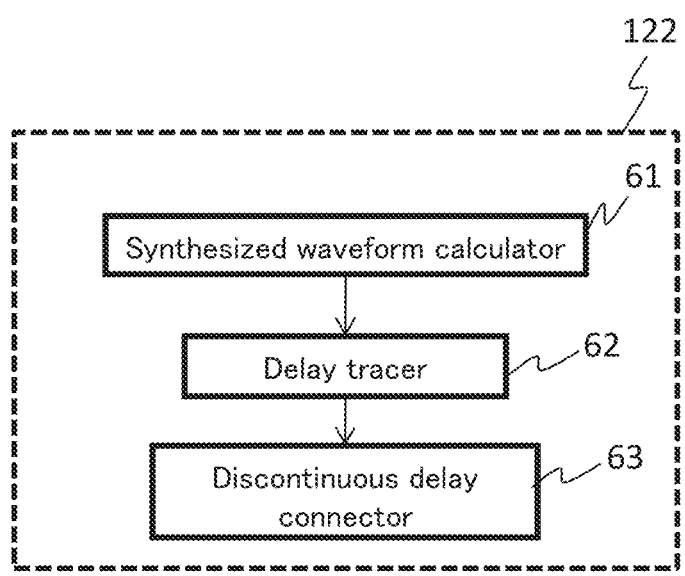

[FIG. 15] A block diagram of the delay time extractor 122 according to the fourth embodiment.

Figure 16:
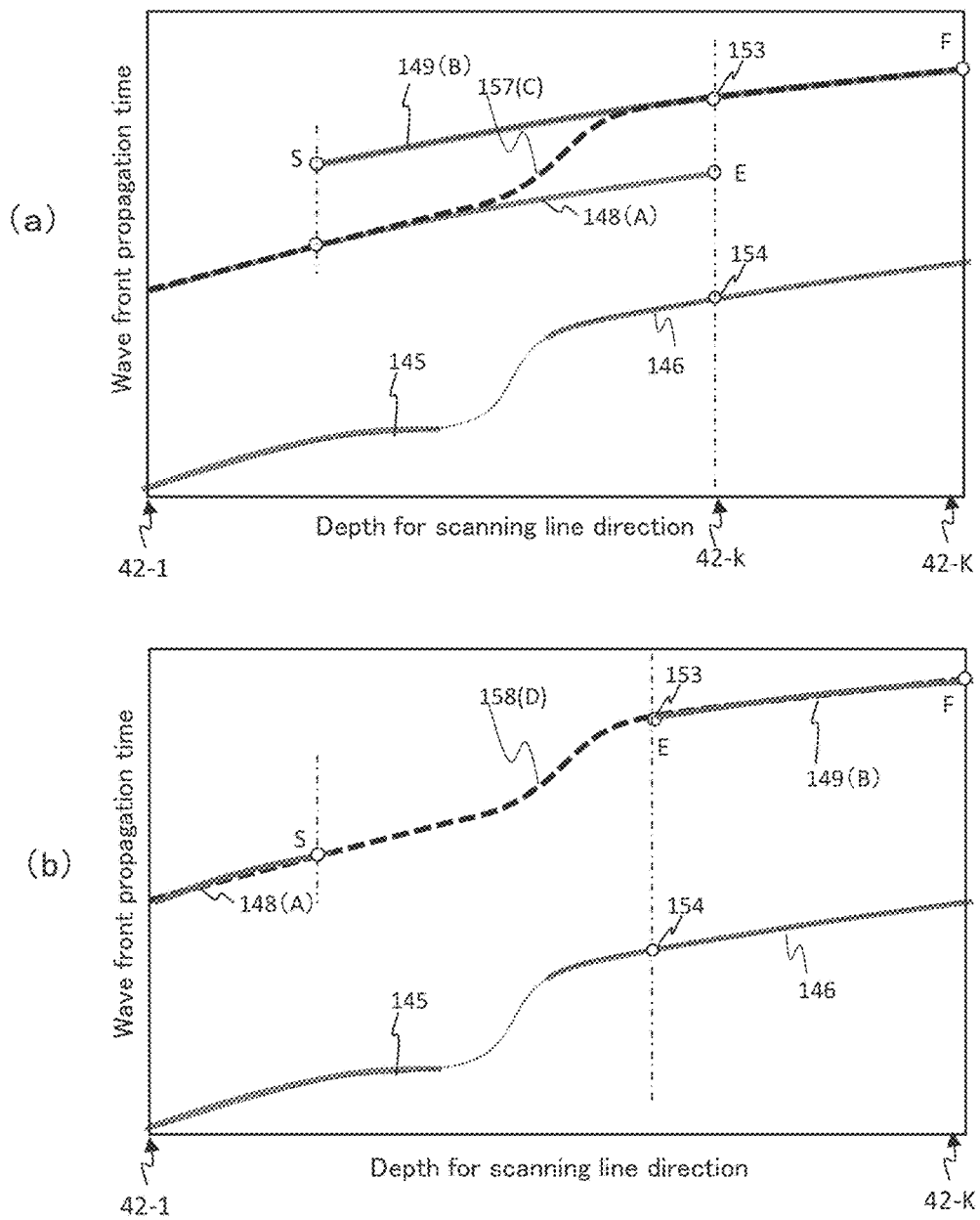

[FIG. 16] FIGS. 16A and 16B: Explanatory drawings showing the delay element lines connected according to the fourth embodiment.

Figure 17:
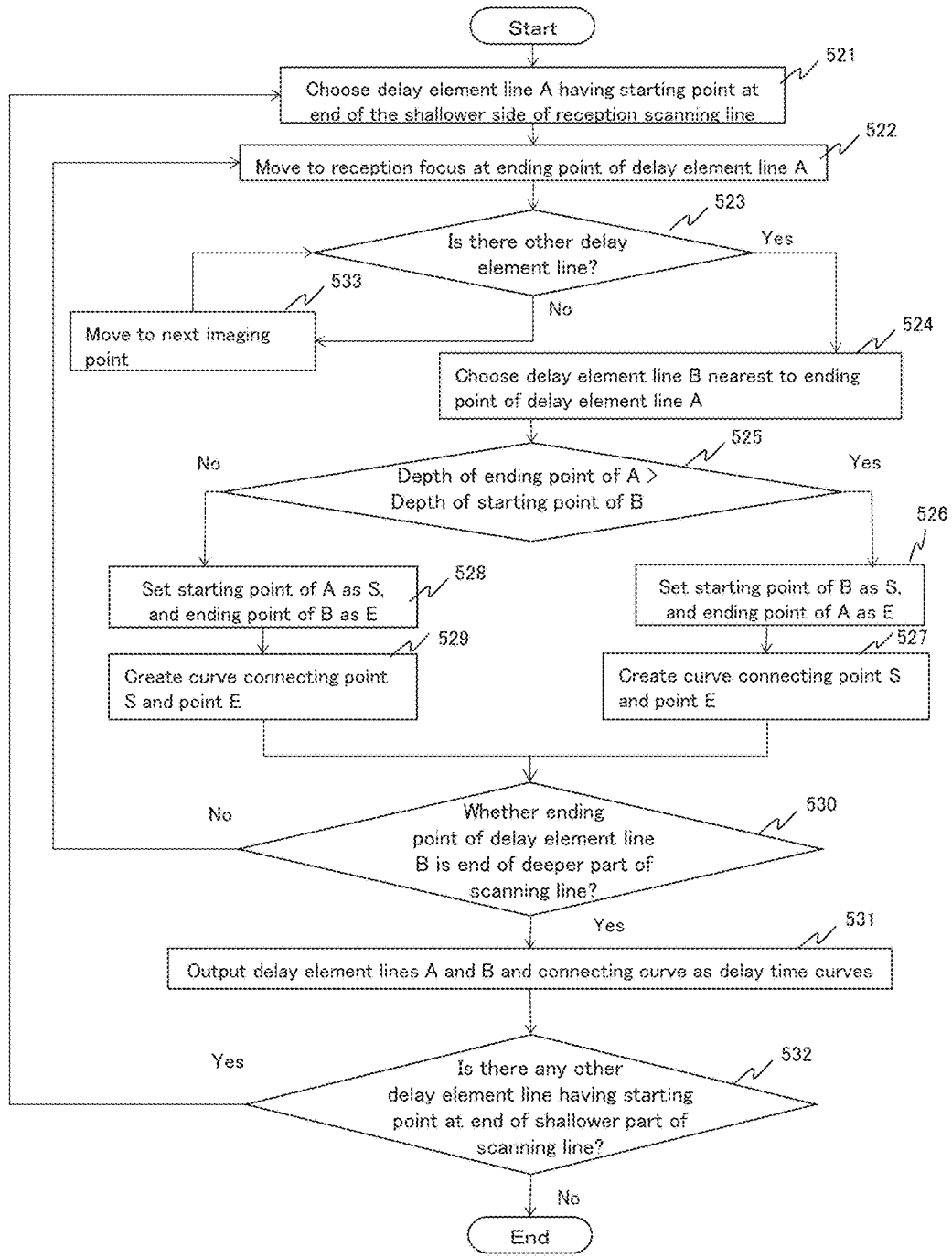

[FIG. 17] A flowchart showing operations of the discontinuous delay connector according to the fourth embodiment.

Figure 18:
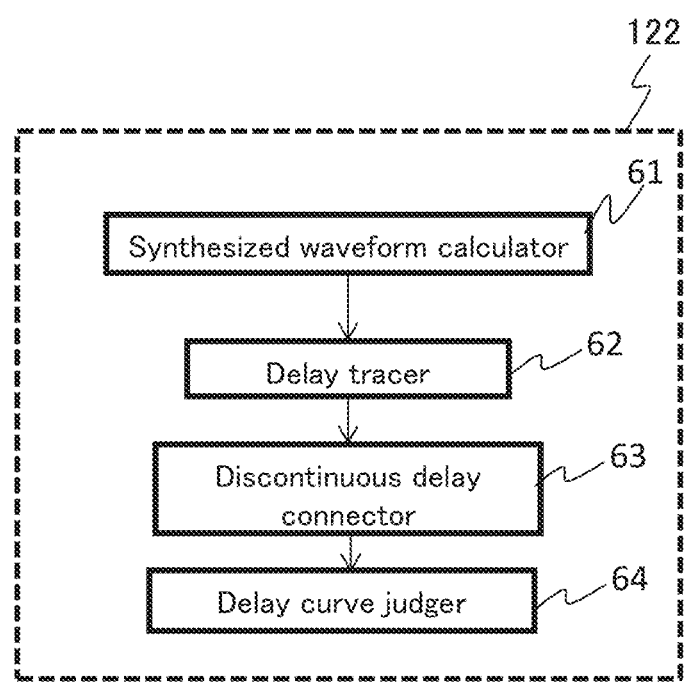

[FIG. 18] A block diagram of the delay time extractor 122 according to the fifth embodiment.

Figure 19:
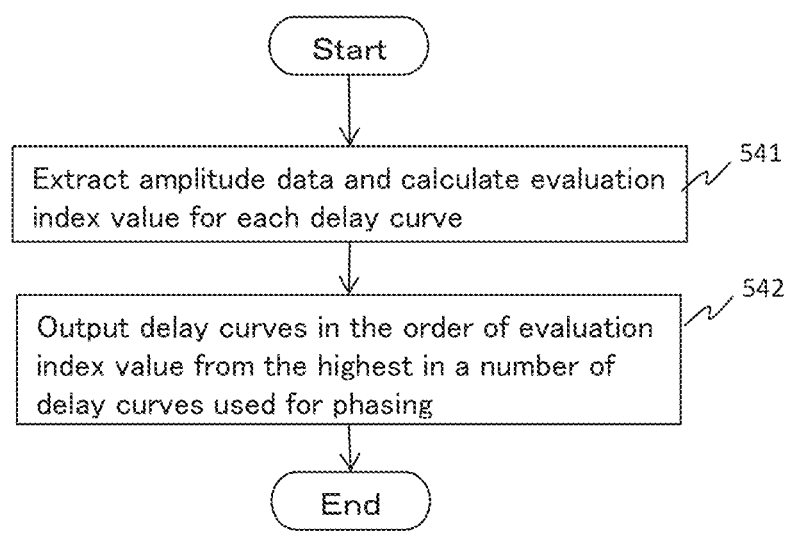

[FIG. 19] A flowchart showing operations of the delay curve judger according to the fifth embodiment.

Figure 20:
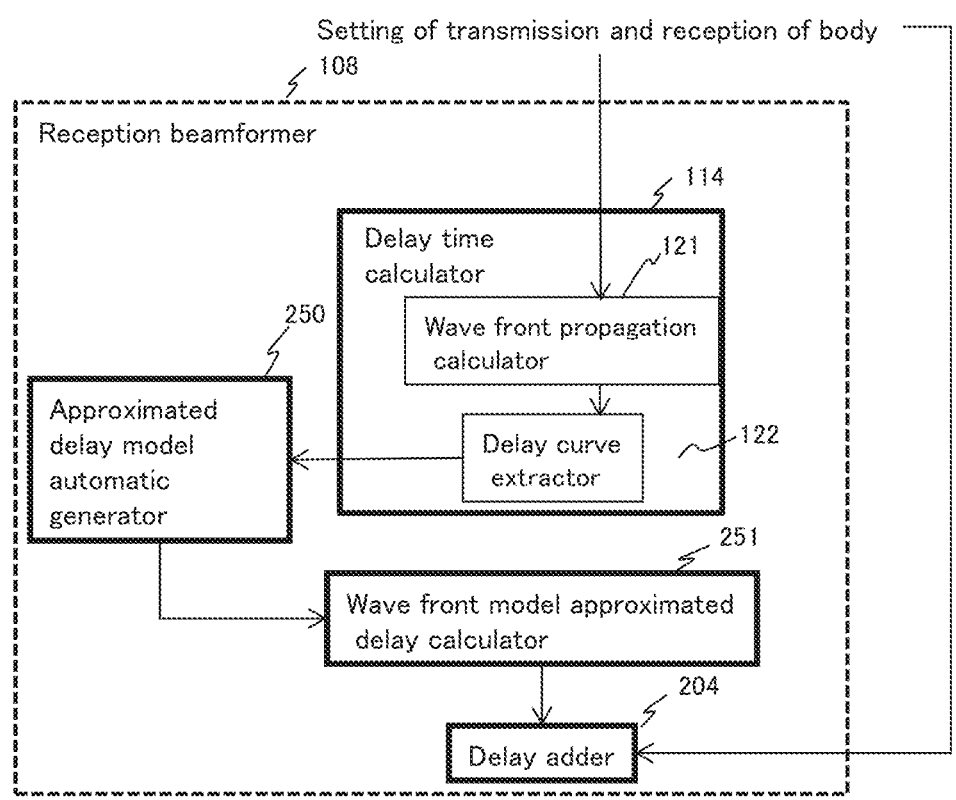

[FIG. 20] A block diagram showing the reception beamformer comprising an approximated delay model automatic generator of the ultrasonic imaging apparatus according to the sixth embodiment.

Figure 21:
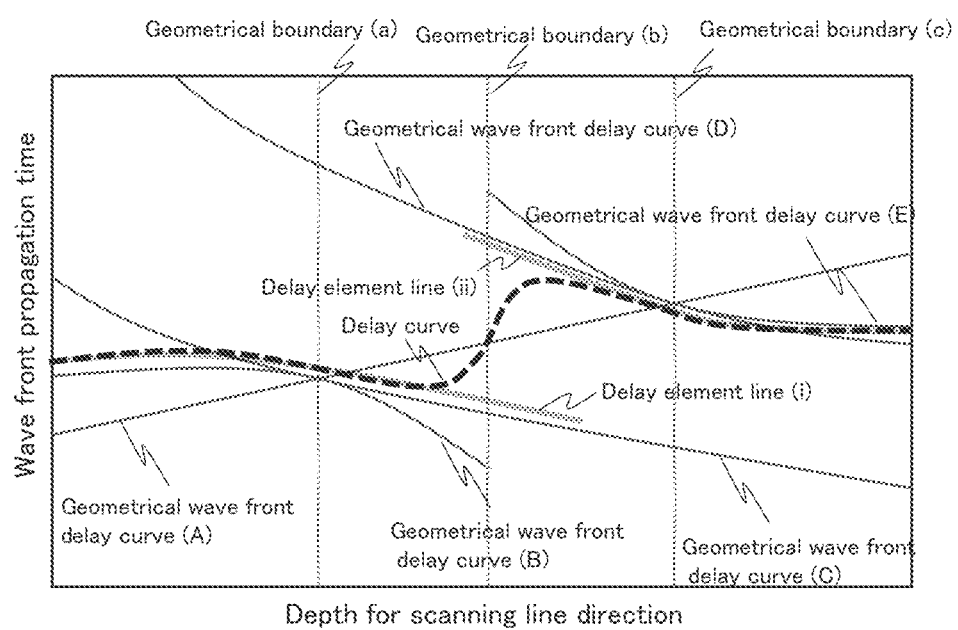

[FIG. 21] An explanatory drawing that exemplifies geometrical constituents used for generation of the approximated delay model in the ultrasonic imaging apparatus according to the sixth embodiment.

Figure 22:
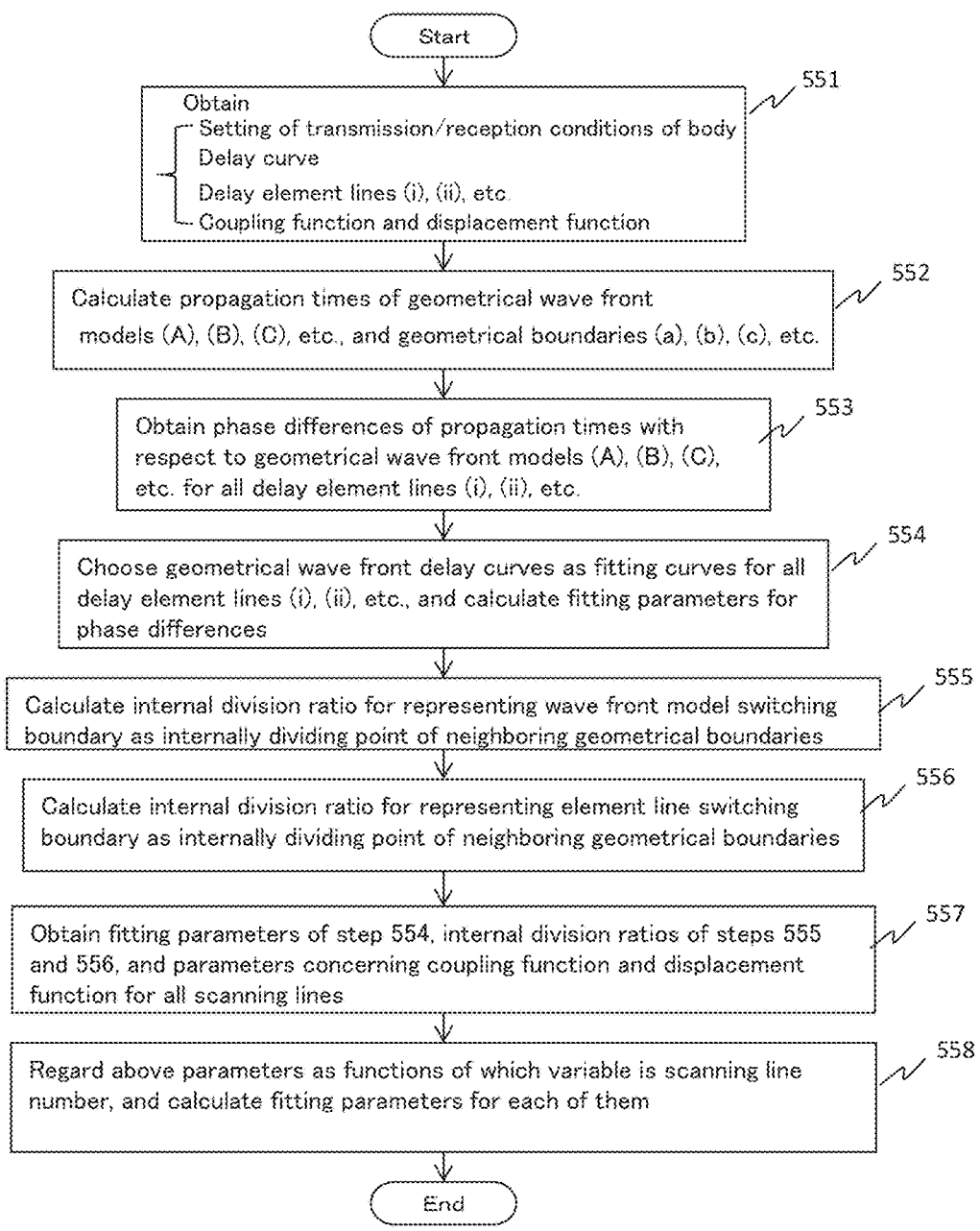

[FIG. 22] A block diagram showing the structure of the approximated delay model automatic generator of the ultrasonic imaging apparatus according to the sixth embodiment.

MODES FOR CARRYING OUT THE INVENTION

Embodiments of the ultrasonic imaging apparatus of the present invention will be explained.

In the ultrasonic imaging apparatus of the present invention, wave front is not approximated with a wave front propagation model obtained with, for example, the virtual sound source method, but times until ultrasonic waves transmitted from a plurality of transmission transducers each arrive at a reception focus are obtained by calculation, and delay times for the reception focus are calculated on the basis of distribution of the obtained arrival times. Therefore, even if the wave front that arrives at the reception focus has a complicated shape, it is not necessary to approximate the wave front, and phasing addition can be carried out with appropriate delay times obtained from times until the ultrasonic waves arrive at the reception focus.

First Embodiment

The ultrasonic imaging apparatus of the first embodiment will be explained with reference to the drawings.

As shown in FIG. 1A, which is a perspective view of the whole ultrasonic imaging apparatus of this embodiment, FIG. 1B, which shows schematic configurations of the same, and FIGS. 2 and 3, which show detailed configurations of parts of the same, the ultrasonic imaging apparatus of this embodiment comprises a transmission beamformer 104 that transmits ultrasonic waves from an ultrasound probe 106 having a plurality of ultrasonic transducers 105 arranged thereon, and a reception beamformer 108.

The transmission beamformer 104 makes a plurality of ultrasonic transducers 105 transmit ultrasonic waves delayed by a predetermined amount for each of the ultrasonic transducers 105 so that they converge at a predetermined transmission focus 41 as shown in FIGS. 4 and 5A. The transmitted ultrasonic waves are, for example, reflected by a subject 100, and received by the ultrasonic transducers 105.

The reception beamformer 108 delays each of the received signals received by the plurality of the ultrasonic transducers 105 by delay times set for each of the plurality of the ultrasonic transducers 105 for the predetermined reception focus 42 (FIGS. 4 and 5A), and then adds them to obtain phased signals. For this purpose, the reception beamformer 108 comprises a delay time calculator 114 that obtains the delay times by calculation. As shown in FIG. 2, the delay time calculator 114 comprises a wave front propagation calculator 121 and a delay time extractor 122. As shown in FIG. 4, the wave front propagation calculator 121 obtains times until the transmitted ultrasonic waves arrive at the reception focus 42 (wave front propagation time, time of flight (TOF)) by calculation for at least a part of the plurality of the ultrasonic transducers 105 that transmit the ultrasonic waves. The delay time extractor 122 calculates delay times for reception focus 42 on the basis of distribution of the arrival times of the ultrasonic waves for each of the plurality of the ultrasonic transducers obtained by the wave front propagation calculator 120.

The wave front propagation times can be calculated from transmission delay times for forming a transmission beam, distances between the ultrasonic transducers and the reception focus at the time of transmission, and acoustic velocity. The delay time extractor 122 chooses one time within the range of the distribution of the wave front propagation times of the ultrasonic waves transmitted from the plurality of the ultrasonic transducers 105 as a wave front propagation time of the forward way (transmission). For example, a time at which the arrival times most concentrate can be chosen. By adding propagation times of the return way (reception) determined according to the distances from the reception focus 42 to each of the ultrasonic transducers 105 to the wave front propagation time of the forward way, delay times for each of the ultrasonic transducers 105 at the time of the reception can be set.

The delay time extractor 122 may also comprises a synthesized waveform calculator 61 that obtains a synthesized waveform of the ultrasonic waves that arrive at the reception focus 42 from the plurality of the ultrasonic transducers 105 (FIG. 6) from distribution of the arrival times of the ultrasonic waves for the reception focus 42 for each of the plurality of the ultrasonic transducers 105 (refer to FIG. 5B). The delay time extractor 122 can also calculate the delay times on the basis of temporal change of the amplitude of the synthesized waveform obtained by the synthesized waveform calculator 61. For example, a propagation time that provides the maximum amplitude value can be chosen as the wave front propagation time of the forward way (transmission).

According to this embodiment, the wave front propagation calculator 122 can obtain the times until ultrasonic waves arrive at the reception focus (wave front propagation times) for all the ultrasonic transducers 105 that transmit the ultrasonic waves before the transmission. Accordingly, the delay times can be calculated in consideration of the wave front propagation times for all the ultrasonic transducers 105 before the transmission, therefore there is no need for modeling of the wave front, and even if the actual wave front has a complicated shape, the delay times can be set for each reception focus with good precision on the basis of propagation times of actual ultrasonic waves.

Hereafter, the ultrasonic imaging apparatus of the first embodiment will be still more specifically explained.

As shown in FIG. 1A, the ultrasonic imaging apparatus comprises an ultrasound probe 106, a body 102 of the apparatus, an image display 103, and a console 110. In the body 102 of the apparatus, as shown in FIG. 1B, there are disposed the transmission beamformer 104, a transmission/reception separation circuit (T/R) 107, the reception beamformer 108, an image processor 109, and a controller 111 that controls operations of these.

The reception beamformer 108 comprises a delay adder 204, the delay time calculator 114, and an aperture synthesiser 205 as shown in FIGS. 1B and 2. The delay time calculator 114 comprises a reception scanning line setter 116, a wave front propagation calculator 121, a delay time extractor 122, and a delay time memory 123. Besides these, there are disposed a beam memory 206 and a frame memory 207, which are used for the aperture synthesis, in the reception beamformer 108.

The transmission beamformer 104 generates signals for transmission beam to be sent to each of the ultrasonic transducers 105. Transmission delay is given to the signals for transmission beam for each of the ultrasonic transducers 105 so that the transmitted beams should converge at a predetermined transmission focus 41 instructed by the controller 111. The signals for transmission beam are sent to the ultrasound probe 106 via the transmission/reception separation circuits 107. The ultrasound probe 106 sends the signals for transmission beam to each of the ultrasonic transducers 105 of the ultrasonic array 101. The ultrasonic transducers 105 transmit ultrasonic waves toward the inside of the body of the subject 100. Echo signals reflected in the body are received by the ultrasonic transducers 105 on the ultrasonic array 101 of the ultrasound probe 106. The received signals pass again through the transmission/reception separation circuit 107, and subjected to phasing addition calculation processing and so forth in the reception beamformer 108.

Operations of the parts of the reception beamformer 108 shown in FIG. 2 will be specifically explained with reference to the flowchart of FIG. 8.

The delay time calculator 112 comprises and is constituted by a processor such as CPU and a memory. The processor reads and executes programs stored beforehand in the memory. Functions of the reception scanning line setter 116, wave front propagation calculator 121, and delay time extractor 122 are thereby realized by software processing as shown in the flowchart of FIG. 8. A part or all of the operations of the delay time calculator 112 can be constituted with ASIC (Application Specific integrated Circuit) or FPGA (Field-Programmable Gate Array), which are hardware, and register.

Before the transmission beamformer 104 performs the ultrasonic signal transmission operation, the controller 111 sends the conditions of transmission of ultrasonic waves, and number and positional information of the reception scanning lines 31 to be set to the reception beamformer 108, and operates it as follows to make it calculate delay times. First, at the time of transmission, the reception scanning line setter 116 of the delay time calculator 112 calculates shape of a region 32 where the transmission beam is irradiated on the basis of the information received from the controller 111, and sets a predetermined number of the reception scanning lines 31 around the region 32 as the center as shown in FIG. 7. It further sets reception focuses 42 in a number of K on the reception scanning lines 31 (step 600). The number of the ultrasonic transducers 105 used at the time of transmission is M.

The wave front propagation calculator 121 calculates time until an ultrasonic wave transmitted from the first ultrasonic transducer 105 arrives at the first reception focus 42 (wave front propagation time) from a certain base time such as time of transmission trigger signal as the base point (steps 601, 602, and 603). As described above, the propagation time is calculated by adding the transmission delay time for the first ultrasonic transducer 105, and time obtained by dividing the geometrical distance between the first ultrasonic transducer 105 and the first reception focus 42 with the acoustic velocity of the ultrasonic wave. The calculated wave front propagation time is stored in the built-in memory. These steps 602 and 603 are successively repeated for K of the reception focuses 42 (steps 604 and 605). Wave front propagation times for K of the reception focuses 42 along the transmission scanning lines 31 are thereby obtained. If the obtained wave front propagation times are plotted with a vertical axis of the wave front propagation time and a horizontal axis of the position of the reception focus 42 (for the depth direction of the reception scanning line), and connected as a curve, one wave front propagation time change curve 55 for the first ultrasonic transducer 105 is obtained as shown in FIG. 5B (step 606).

By repeating this operation for all the ultrasonic transducers 105 (in a number of M), M of wave front propagation time curves 55 for each of M of the ultrasonic transducers 105 are obtained as shown in FIG. 5B (steps 607 and 608).

As clearly seen from FIG. 5B, the wave front propagation times until ultrasonic waves from all the ultrasonic transducers 106 arrive at the certain reception focus 42 are distributed for the time direction, but there are differences in the distribution density. Therefore, the delay time extractor 122 can determine the delay time for one reception focus 42 by choosing (extracting) one arrival time (delay time) within the distribution range of the wave front propagation time change curves 55 for the one reception focus 42 (steps 609 and 610). By repeating this operation for all the reception focuses (in a number of K), and connecting all the delay times as a curve, a delay time curve 43 can be obtained by calculation (steps 611 and 612).

Then, the delay time extractor 122 adds arrival times of the ultrasonic waves from the reception focus 42 to the ultrasonic transducers 105 at the time of reception (wave front propagation times of return way) to the delay times of the obtained delay time curve 43 to calculate the delay times for each of the ultrasonic transducers 105 at the time of reception, and stores them in the delay time memory 123 (steps 613, 614, and 615). The wave front propagation times of the return way can be calculated by dividing geometrical distances between the reception focus 42 and the ultrasonic transducers 105 with the acoustic velocity of the ultrasonic waves.

The processings of the aforementioned steps 600 to 615 are repeated for all the reception scanning lines set by the reception scanning line setter 116 for one time of transmission, and delay times for the reception focuses 42 for all the reception scanning lines are stored in the delay time memory 123.

If all the delay times are stored in the delay time memory 123, the controller 11 makes the transmission beamformer 104 transmit the ultrasonic signals. As a result, ultrasonic waves are transmitted from each of the ultrasonic transducers 105 toward the subject 100. Ultrasonic echoes reflected in the subject 100 are received by the plurality of the ultrasonic transducers 105.

The delay adder 204 delays the received signals by the delay times stored in the delay time memory 123 for each of the reception transducers for each of the ultrasonic transducers 105, and then adds them to obtain phased signals. This operation is repeatedly performed for all the reception focuses 42 on the reception scanning lines 31. The phased signals obtained for the reception focuses 42 on each of the reception scanning lines 31 are stored in the beam memory 206. If this operation is repeated for all the reception scanning lines 31, and the phased signals for all the reception scanning lines 31 are stored in the beam memory 206, the process is returned to the step 600, and the next transmission is performed.

The aperture synthesiser 205 performs aperture synthesis by reading a plurality of phased signals obtained by different transmissions for the same reception focus 42 from the beam memory 206, and synthesizing them. Then, an image of imaging region is generated by using the synthesized phased signals. The generated image is stored in the frame memory 207, and outputted to the image processor 109. The image processor 109 displays the image on the image display 103, after image processing is performed as required.

As described above, in this embodiment, wave front propagation times from all the ultrasonic transducers 105 at the time of transmission to the reception focus 42 are calculated, and the delay times for the reception focus 42 are chosen (extracted) according to the distribution of the wave front propagation times for the time direction. Therefore, geometrical modeling of wave front is not required, and even if transmission beamforming is performed for a complicated wave front shape, delay times adapted to actual wave front propagation can be set from such transmission/reception conditions as positions of ultrasonic transducers and transmission delay times. As a result, the energy of the transmission beam can be efficiently received, and SN ratio can be improved.

Further, according to this embodiment, even for the outside of the region 32 where transmission beam is directly irradiated, in which the wave front shape becomes complicated, the delay time can be calculated, and therefore reception scanning lines 31 can be set as shown in FIGS. 5A and 7. Accordingly, the region for which phasing can be performed is expanded to the outside of the transmission beam irradiation region 32, unlike the conventional virtual sound source method and so forth, and it becomes possible to obtain a higher frame rate.

In addition, the delay time extractor 122 can use an arbitrary method for extracting one delay time for the one reception focus 42 in the step 610. For example, a synthesized waveform of the ultrasonic waves that arrive at one reception focus 42 from a plurality of the ultrasonic transducers 105 may be obtained from distribution of the arrival times of the ultrasonic waves for each of a plurality of the ultrasonic transducers 105 with the synthesized waveform calculator 61 in the delay time extractor 122 (FIG. 3) as shown in FIG. 6. In such a case, it becomes possible to calculate the delay times on the basis of temporal change of the amplitude of the synthesized waveform in the step 610. This technique will be further explained.

In the step 603, the synthesized waveform calculator 61 of the delay time extractor 122 calculates a synthesized waveform obtainable by adding transmission waveforms of a plurality of the ultrasonic transducers 105 in accordance with the equation (1) using the wave front propagation times obtained for each of the plurality of the ultrasonic transducers 105. In the equation (1), p is an amplitude value of waveform of ultrasonic wave transmitted from each of the ultrasonic transducers 105. The value of p is given to the delay time extractor 122 from the controller 111 as one of the transmission conditions. $\tau(m)$ is wave front propagation time of the m-th ultrasonic transducer 105. By shifting the phase of the ultrasonic waveform by the wave front propagation time $\tau(m)$ obtained in the step 603 for each of the ultrasonic transducer 105 in accordance with the equation (1), and adding the amplitude p of the ultrasonic waveform for M of the ultrasonic transducers 105, a synthesized waveform $p_{sum}$ for one reception focus 42 can be calculated (refer to FIG. 6).

[Equation 1]

$$P_{sum} = \sum_{M} p(t - \tau(m))/M \qquad (1)$$

The delay time extractor 122 can choose an arrival time that provides the maximum or local maximum of the amplitude of the synthesized waveform shown in FIG. 6 as the delay time.

Further, the synthesized waveform calculator 61 can obtain such a distribution map showing change of intensity distribution of the amplitude of the synthesized waveform along the depth direction of the scanning line as shown in FIG. 9 by performing the calculation of the equation (1) for all the reception focuses on the reception scanning lines. Therefore, in the step 610, the delay time extractor 122 can also draw a delay time curve by continuously choosing the wave front propagation times for the direction of the reception scanning line using the intensity distribution map of the amplitude of the synthesized waveform shown in FIG. 9.

The amplitude of the synthesized waveform of FIG. 9 substantially corresponds to amplitude value of a phased signal that is assumed to be obtained when a certain wave front propagation time is chosen as the delay time and phasing addition is performed by using the delay time. Therefore, in the extraction of delay time curve in the step 610, it becomes possible to evaluate the value of the delay time on the basis of the intensity value of the amplitude of the synthesized waveform shown in FIG. 9. That is, for example, a higher evaluation score can be given to a delay time that provides a phased signal of a larger amplitude. Therefore, it becomes possible to perform a feedback processing of the selection of the delay time using that evaluation. Accordingly, even in transmission beamforming in which modeling of the wave front is difficult, optimal delay calculation can be performed. This technique will be specifically explained in the explanation of the fifth embodiment.

FIGS. 5B and 9 show examples of distributions of the wave front propagation time and the intensity of the amplitude of the synthesized waveform at the time of performing transmission beamforming with a single transmission focus 41. In FIG. 5A, regions to which the virtual sound source model can be applied (shallow part and deep part of virtual sound source region), and the outside of the virtual sound source region to which the virtual sound source model cannot be applied are shown. The virtual sound source region is the same as the sandglass-shaped geometrical region formed with straight lines connecting the ends of a plurality of the ultrasonic transducers 105 (aperture) used at the time of transmission and a focus, i.e., the transmission beam direct irradiation area 32.

As a comparative example, a delay time curve was obtained with a reception beamformer comprising a calculator that calculates delay time with a wave front model based on the virtual sound source method as shown in FIG. 3A. The results are shown in FIGS. 5B and 9. It can be seen that, as shown in FIG. 5B, the delay time curve 56 calculated with the wave front model based on the virtual sound source method significantly deviates from the distribution of the wave front propagation time change curves 55 obtained according to this embodiment, and the intensity distribution of the amplitude of the synthesized waveform shown in FIG. 9 in the outside of the virtual sound source region. Further, it is apparently seems that, in the shallow part and deep part of the virtual sound source region, the delay time curve 56 based on the virtual sound source method meets the end of the distribution of the wave front propagation time change curve 55 as shown in FIG. 5B, but it deviates from the maximum of the intensity distribution of the amplitude of the synthesized waveform as clearly seen from FIG. 9. Therefore, the amplitudes of the phased signals obtainable by using the delay time curve 56 based on the virtual sound source method become smaller than the amplitudes of the phased signals obtainable by using the delay times of this embodiment.

Second Embodiment

The ultrasonic imaging apparatus of the second embodiment will be explained.

According to the second embodiment, when the delay time extractor 122 generates a synthesized waveform by adding the transmission waveforms of a plurality of the ultrasonic transducers 105 in the step 610 of FIG. 8 shown for the first embodiment, it obtains frequency distribution of the arrival times of the ultrasonic waves for each of the plurality of the ultrasonic transducers, and generates a synthesized waveform by using the frequency distribution. Calculation amount is reduced by this technique.

This technique will be specifically explained with reference to FIG. 10. The delay time extractor 122 continuously sets N (N<M) of time ranges of a predetermined width for the wave front propagation times for each of the plurality of the ultrasonic transducers for the reception focus obtained in the step 603 of the first embodiment (wave front propagation time change curve 55, FIG. 10A) as shown in FIG. 10B, and counts the numbers of the wave front propagation times (wave front propagation time change curve 55) included in the time ranges to calculate the frequency distribution as shown in FIG. 10B. In this explanation, the frequency distribution is represented as a histogram as an example. The distribution of the example shown in FIG. 10B is a distribution in which as the wave front propagation time becomes smaller, the frequency becomes higher.

For the obtained frequency distribution function (histogram) shown in FIG. 10B, if the number of the wave front propagation times included in the n-th time range is represented as $h(t_n)$, the amplitude $P_{sum}$ of the synthesized waveform can be calculated in accordance with the equation (2) using the amplitude p of the ultrasonic waveform. $t_n$ is a representative value of the wave front propagation time of the n-th time range (for example, either one of the maximum, minimum and average values). M represents the number of the ultrasonic transducers 105 used for the transmission.

[Equation 2]

$$P_{sum} = \sum_{N} h(t_n) \times p(t - t_n)/M \qquad (2)$$

Comparing the equations (1) and (2), it can be seen that the number for the addition is the number M of the ultrasonic transducers in the equation (1), but it is the number N (N<M) of the time ranges in the equation (2). Therefore, the calculation amount of the calculation method of the synthesized waveform using the equation (2) can be reduced compared with that of the case using the equation (1). In addition, practically sufficient temporary change of the amplitude of the synthesized waveform can be obtained. Therefore, the calculation load at the time of calculating the synthesized waveform can be reduced, calculation cost of ultrasonic diagnostic apparatuses can be reduced, and an actually implementable algorithm can be realized.

The configurations and operations of the ultrasonic imaging apparatus of the second embodiment other than those explained above are the same as those of the first embodiment, and therefore explanations thereof are omitted.

Third Embodiment

The ultrasonic imaging apparatus of the third embodiment will be explained with reference to FIGS. 11 and 12.

In the third embodiment, the delay time extractor 122 comprises a delay tracer 62 in addition to the synthesized waveform calculator 61 explained for the first embodiment. The delay tracer 62 extracts one or more delay time curves by tracing extremes of the intensity distribution (temporary change curve) of the amplitude of the synthesized waveform of the ultrasonic waves obtained by the synthesized waveform calculator 61 in the direction of the reception scanning line.

First, the synthesized waveform calculator 61 calculates the intensity distribution of the amplitude of the synthesized waveform of the ultrasonic waves along the direction of the scanning line as explained for the first embodiment (refer to FIG. 9).

Then, as shown in the flowchart of FIG. 12, the delay tracer 62 obtains a wave front propagation time at which the amplitude value of curve which indicates the change of the amplitude value of the synthesized waveform in the direction of the wave front propagation time (refer to FIG. 6) becomes an extreme at one reception focus 42 on the reception scanning line. This operation is performed for all the reception focuses on the reception scanning line (step 501).

Then, as shown in FIG. 13, significantly large amplitude values among the extremes obtained in the step 501 are extracted as delay element points (step 502). Specifically, for example, when amplitude value of an extreme is not smaller than a preset minimum amplitude value, or ratio of amplitude value of an extreme to the maximum amplitude value among extremes for that reception focus is not smaller than a preset minimum ratio, the extreme is extracted as a delay element point. One or more delay element points are thereby extracted for almost all the reception focuses.

By successively tracing the extracted delay element points along the reception scanning line as shown in FIG. 13, a continuous delay element line is extracted. Specifically, for example, the tracing is started from a delay element point 131 of the reception focus 42-1 at the end on the side of shallower part of the reception scanning line (side of the ultrasound probe 116) (step 503), then a tracing vector 141 that connects the delay element point 131 with a delay element point 132 of the nearest propagation time at the following reception focus 42-2 is set, and inclination of the tracing vector 141 is calculated (step 504). When the inclination of the tracing vector 141 is not larger than a set value defined beforehand, a tracing line that connects the delay element point 131 and the delay element point 132 is set, and the tracing ending point 132 is set as a new tracing starting point (step 506). Further, a delay element point 151 that has not been set as a starting point yet for the current reception focus 42-1 is set as a tracing starting point (step 507), the process is returned to the step 504, a tracing vector 142 that connects the starting point with the nearest delay element point 152 at the following reception focus 42-2 is set, and when the inclination of the tracing vector is not larger than the set value, a tracing line is set (steps 504, 505, and 506). When the tracing is completed for all the delay element points for the current reception focus 42-1, setting of tracing lines is repeated by using delay element points 132 and 152 of the following reception focus 42-2 as the starting points.

When inclination of a tracing vector is larger than the preset value in the step 505, it is judged to be a discontinuous crest line, and the tracing is ended at that delay element point that is thus a tracing ending point (step 508). The tracing lines from the tracing starting point to the tracing ending point are extracted as delay element lines (step 509). Continuous delay element lines 145, 146, and 147 are thereby extracted.

Among the extracted delay element lines, the delay element line 147 that continues from the reception focus 42-1 on the shallowest side of the reception scanning line to the reception focus 42-K on the deepest side is chosen, and used as a delay time curve.

As described above, according to this embodiment, by extracting all delay element points having significant amplitude values, and tracing them, a delay time curve can be set. If phased signals are obtained by using this delay time curve, it becomes possible to use wave front energy that has not conventionally been used for phasing for imaging, and therefore SN ratio can be improved.

When there are a plurality of the delay element lines 147 that continue from the reception focus 42-1 to the reception focus 42-K, any one of them can be chosen and used.

There can also be employed a configuration that, as shown in FIG. 14, the reception beamformer 108 comprising a plurality of delay adders 204-1 and 204-2 in parallel is used, the plurality of the delay adders 201-1 and 204-2 perform a delay processing for the same received signal with different delay times, respectively, by using each of the plurality of delay element lines as delay time curve to obtain phased signals. In this case, the outputs of the plurality of the delay adders 201-1 and 204-2 are added and used. It is thereby made possible to perform the delay processing by using delay time curves of the maximum number that can be set in one time of transmission/reception and reception beamforming, and an effect equivalent to that of the case where phasing is performed for each of a plurality of wave fronts can be obtained. Therefore, by generating an ultrasonogram using signals obtained by adding phased signals outputted by a plurality of delay adders, higher resolution can be realized by the multi-look effect.

The configurations and operations other than those described above are the same as those of the first embodiment, and therefore explanations thereof are omitted.

Fourth Embodiment

The ultrasonic imaging apparatus of the fourth embodiment will be explained.

The ultrasonic imaging apparatus of this embodiment has the same configurations as those of the third embodiment, except that the delay time extractor 122 further comprises a discontinuous delay connector 63 as shown in FIG. 15. As shown in FIG. 16, the discontinuous delay connector 63 connects delay element lines 145, 146, 148, and 149 extracted by the delay tracer 62, when they are discontinuous, to generate a delay element line 147 that continue from the reception focus 42-1 on the shallowest side to the reception scanning line to the reception focus 42-K on the deepest side.

First, delay element line A 148 and delay element line B 149 to be connected by the discontinuous delay connector 63 are chosen. Specifically, as shown in FIG. 16A, one of delay element lines 145 and 148 starting from the reception focus 42-1 on the shallowest side of the reception scanning line is first chosen as the delay element line A (step 521). Then, the reception focus 42-$k$ as the ending point of the selected delay element line A is considered, and if there are other delay element points 153 and 154, the delay element point 153 of the nearest wave front propagation time among them is chosen, and the delay element line 149 to which the delay element point 153 belongs is set as the delay element line B (steps 522, 523, and 524). If there are no other delay element points, the above operation is performed for the next reception focus, and the operation is repeated for the following reception focuses until other delay elements are found (step 533).

Then, a new delay element line for continuously connecting the delay element lines A and B is generated. First, it is judged whether depth of the reception focus at the ending point of the delay element line A is larger than that of the reception focus at the starting point of the delay element line B, that is, whether there is an overlapping part for the delay element lines, as shown in FIG. 16A (step 525).

In the step 525, when the depth of the reception focus at the ending point of the delay element line A is larger than that of the reception focus at the starting point of the delay element line B, and thus the delay element lines A and B have an overlapping part (FIG. 16A), the starting point of the delay element line B is defined to be S, the ending point of the delay element line A is defined to be E (step 526), and a connection curve C 157 that continuously connects the delay element line A and the delay element line B between the reception focus of the point S and the reception focus of the point E is generated. Specifically, by using a displacement function f(d) (d represents depth) defined beforehand, of which orbit is asymptotic to 0 at the depth of the reception focus of the point S and asymptotic to 1 at the depth of the reception focus of the point E, wave front propagation time C(d) of the connection curve 157 is calculated in accordance with the equation (3). In the equation (3), A(d) is the wave front propagation time of the delay element line A, and B(d) is the wave front propagation time of the delay element line B.

$$C(d)=A(d)*(1-f(d))+B(d)*f(d) \qquad (3)$$

By calculating the equation (3), the connection curve C 157 is generated (step 527).

On the other hand, when depth of the reception focus at the ending point of the delay element line A is smaller than that of the reception focus at the starting point of the delay element line B in the step 525, and therefore the delay element lines A and B do not have any overlapping part as in the case shown in FIG. 16B, the ending point of the delay element line A is defined to be S, the starting point of the delay element line B is set to be E (step 528), and a connection curve D 158 that continuously connects the delay element line A and the delay element line B between the reception focus of the point S and the reception focus of point E is generated. As for the connection curve D158, a coupling function of which orbit shares a tangent with the delay element line A at the ending point S of the delay element line A, and shares a tangent with the delay element line B at the starting point E of the delay element line B is obtained by calculation, and the connection curve D158 is generated by using the coupling function (step 529).

Then, when the ending point F of the delay element line B is the deepest reception focus 42-K (end on the deeper side of the reception scanning line), delay element lines A and B, and the connection curve C or D that connects the delay element lines A and B are outputted as the delay time curves (steps 530 and 531). Then, when any delay element line starting from the reception focus 42-1 on the shallowest side of the reception scanning line still remains, the process is returned to the step 521, and the aforementioned processing is repeated (step 532).

When the ending point F of the delay element line B is not the deepest reception focus 42-K (end on the deeper side of the reception scanning line), the process is returned to the step 522 to repeat the processing of connecting with the following delay element line for the delay element line B instead of the delay element line A (step 530).

By repeating the processing of connecting the delay element line A or B with the connection curve C or D as described above, a delay curve continuing from the reception focus 42-1 on the shallowest side of the reception scanning line to the reception focus 42-K on the deepest side can be generated. By repeating this processing for all the delay element lines that start at the reception focus starting position, one or a plurality of delay curves can be generated.

As a result, even when the delay element line is discontinuous, a delay curve that can minimize degradation of image due to discontinuity of the delay curve can be generated.

It is also possible to generate a plurality of delay time curves, and set them in such a plurality of delay adders 204-1 and 204-2 as shown in FIG. 14, respectively.

The other configurations and operations are the same as those of the third embodiment, and therefore the explanations thereof are omitted.

Fifth Embodiment

The ultrasonic imaging apparatus of the fifth embodiment will be explained with reference to FIGS. 18 and 19.

As shown in FIG. 18, the ultrasonic imaging apparatus of the fifth embodiment comprises a delay curve judger 64 in the delay time extractor 122. When there are a plurality of delay time curves extracted or generated as described for the third or fourth embodiment, the delay curve judger 63 calculates evaluation index values of the curves, which represent degree of suitability for use in the phasing addition, by using amplitude data of synthesized waveform as the wave front propagation time of each of the delay time curves (refer to FIG. 9). Then, when there is one delay adder 204 as shown in FIG. 1, a delay time curve that provides the highest evaluation index value is chosen, or when a plurality of the delay adders 204 are disposed as shown in FIG. 14, the delay time curves in the same number as the number of the delay adders are chosen in the order of the evaluation index value from the highest, and outputted to the delay adder 204.

Specifically, as shown in the flowchart of FIG. 19, all the amplitude value data on the delay time curves are first extracted from the intensity distribution of the amplitude of the synthesized waveform shown in FIG. 9 for all the delay curves. All the extracted amplitude value data are processed with an evaluation function defined beforehand to calculate the evaluation index values (step 541). As for the evaluation function, for example, total or average value of all the extracted amplitude values, a value obtained by adding the extracted amplitude values weighted with weights set for each of the reception focuses, or the like can be used.

Then, the delay curves are ranked in the order of the value of the evaluation function calculated in the step 541 from the highest, and the delay curves in a number of the delay curves used in the reception beamforming are outputted to the delay adder 204 (step 542).

As a result, the delay adder 204 can perform delay addition by using optimal delay time curves in a required number, therefore energy of the wave front can be efficiently received, and the SN ratio can be improved.

Sixth Embodiment

The sixth embodiment will be further explained with reference to FIGS. 20, 21, and 22. FIG. 20 is a block diagram showing the reception beamformer having an approximated delay model automatic generator, FIG. 21 is a drawing exemplifying geometrical constituent elements used for generation of an approximated delay model, and FIG. 22 is a block diagram showing the structure of the approximated delay model automatic generator.

As shown in FIG. 20, the ultrasonic imaging apparatus of the sixth embodiment comprises an approximated delay model automatic generator (part for automatically generating approximated delay model) 250. The approximated delay model automatic generator 250 obtains data of delay curves calculated by the delay time calculator 114 similar to that of any one of the first to fifth embodiments, and constructs a constitutive equation for calculating an approximated curve of the delay curve calculated by the delay time calculator 114 from the correlation of a plurality of geometrical wave front models and geometrical constraints prepared beforehand, and the delay time calculated by the delay time calculator 114. It is thereby made possible to automatically generate a delay time from an approximated delay model common to the same imaging conditions or transmission conditions without generating delay time curves with the delay time calculator 114 for a plurality of the reception scanning lines just before the transmission for every transmission.

Specifically, as shown in FIG. 22, there are obtained the delay time curves calculated by the delay time calculator 114, the delay element lines (i), (ii), and so forth used for the calculation of delay time curves by the delay time calculator 114 in the second to fifth embodiments, the displacement function or coupling function used in the steps 527 and 529 mentioned in FIG. 17, and the transmission/reception conditions (step 551).

Then, from the transmission/reception conditions, propagation times of geometric wave front models (A), (B), (C) prepared beforehand as shown in FIG. 21, such as wave fronts of virtual sound source wave, plane wave, and transducer spherical wave etc., and geometrical boundaries (a), (b), (c) as geometrical constraints, such as focal distances and boundaries of transmitted beam irradiation regions, are calculated (step 552).

Then, in order to construct the constitutive equation for calculating approximated curves of the delay element lines (i), (ii), and so forth, phase differences with respect to all the geometric wave front delay curves are calculated for each of the delay element lines (step 553).

For all the delay element lines (i), (ii), and so forth, a geometrical wave front curve that gives the minimum phase difference is chosen as a fitting curve for every reception focus, and then fitting parameters of a polynomial curve, for example, are calculated for the phase difference with respect to the fitting curve (step 554).

Further, in order to calculate a constitutive equation for obtaining a wave front model switching boundary where the geometrical wave front delay curve used as the fitting curve is changed, for example, an internal division ratio used when the boundary is represented as a internally dividing point of neighboring geometric boundaries is calculated (step 555).

Furthermore, in order to calculate a constitutive equation for obtaining an element line switching boundary where the delay curve moves from one delay element line to another delay element line, for example, an internal division ratio used when the boundary is represented as a internally dividing point of neighboring geometric boundaries is calculated (step 556).

The aforementioned fitting parameter, internal division ratio of the wave front model switching boundary, internal division ratio of the element line switching boundary, and parameters concerning the coupling function and displacement function obtained by the delay curve extractor are referred to as approximated delay constituent parameters. The approximated delay constituent parameters are then calculated for all the scanning lines of one time of transmission (step 557).

The aforementioned parameters are regarded as functions of which variable is the scanning line number, and fitting parameters used for fitting these functions to, for example, a polynomial curve, are calculated (step 558). The fitting parameters of the approximated delay constituent parameters calculated above are sent to a wave front model approximated delay calculator.

In the wave front model approximated delay calculator 251, with the aforementioned fitting parameters of the approximated delay constituent parameters, approximated delay constituent parameters are calculated for every scanning line, and with these approximated delay constituent parameters, and geometrical wave front delay curves and geometric boundaries calculated beforehand, an approximated delay curve of the optimal delay curve is calculated.

As a result, the delay time obtained by the delay time calculator 114 similar to those of the first to fifth embodiments can be approximated to an approximated delay model constituted by a geometrical wave front model, and the calculation can be performed with a calculation amount equivalent to that of the delay calculation performed with the conventional reception beamformer shown in FIG. 3A. Therefore, imaging can be performed with image quality equivalent to that obtainable with the delay time according to any one of the first to fifth embodiments with suppressing the calculation amount.

The ultrasonic imaging apparatuses of the embodiments explained above have a configuration that the delay time calculator 114 is provided in the inside of the body 102 of the apparatus, but the whole delay time calculator 114 or the whole reception beamformer 108 may also be provided as an apparatus separate from the body 102 of the apparatus. In such a case, the delay time calculator 114 or the reception beamformer 108, and the body 102 of the apparatus are connected via a signal wire or a network. For example, the whole delay time calculator 114 or reception beamformer 108 is implemented in a common computer or a calculation apparatus such as workstation, and connected with the body 102 of the ultrasonic imaging apparatus via a network. The delay time calculator 114 is made to have a configuration that it receives transmission conditions and so forth via a network, calculates delay times, and transmits them to the ultrasonic imaging apparatus as a client terminal. When the reception beamformer 108 is provided as an apparatus separate from the body 102 of the apparatus, it receives received signals via a network, generates aperture-synthesized phased signals, and transmits them to the body 102 of the apparatus via a network. It is thereby made unnecessary to mount the delay time calculator 114, which requires comparatively large calculation amount, on the body 102 of the ultrasonic imaging apparatus. As a result, phasing addition can be performed with delay times based on wave front propagation times for every ultrasonic transducer, and image quality can be improved even with a small and simple ultrasonic imaging apparatus.

DESCRIPTION OF NOTATIONS

100 Subject
101 Ultrasonic element array
102 Body of ultrasonic imaging apparatus
103 Image display
104 Transmission beamformer
106 Ultrasound probe
107 Transmission/reception separation circuit (T/R)
108 Reception beamformer
109 Image processor
110 Console
111 Controller

The invention claimed is:

1. An ultrasonic imaging apparatus, comprising:
a transmission beamformer that causes a plurality of ultrasonic transducers to transmit ultrasonic waves that are delayed by a predetermined transmission delay time to form a predetermined transmission beam; and
a reception beamformer that delays received signals by delay times set for each of the plurality of the ultrasonic transducers, after receiving ultrasonic waves transmitted by the plurality of the ultrasonic transducers for a predetermined reception focus, and adds the delayed received signals to obtain phased signals,
wherein the reception beamformer comprises a delay time calculator that obtains the delay times by calculation,
wherein the delay time calculator comprises a wave front propagation calculator that, for each of the plurality of ultrasonic transducers, calculates arrival times of ultrasonic waves transmitted from each of the plurality of ultrasonic transducers to the reception focus based on the predetermined delay time, a distance between the respective transducer and the reception focus and a velocity of the ultrasonic wave, and a delay time extractor that calculates the delay times based on a distribution of the calculated arrival times of the ultrasonic waves for each of the plurality of the ultrasonic transducers obtained by the wave front propagation calculator,
wherein the delay time extractor obtains a synthesized waveform of the ultrasonic waves that arrive at the reception focus from the plurality of the ultrasonic transducers based on the distribution of the calculated arrival times of the ultrasonic waves for each of the plurality of the ultrasonic transducers, and calculates the delay times based on a temporal change of amplitude of the synthesized waveform, and
wherein the delay time extractor obtains a frequency distribution of the calculated arrival times of the ultrasonic waves obtained by the wave front propagation calculator for each of the plurality of the ultrasonic transducers, and calculates the synthesized waveform by using the obtained frequency distribution.

2. The ultrasonic imaging apparatus according to claim 1, wherein the delay time calculator comprises a reception scanning line setter that sets a reception scanning on which the reception focus is set,
the wave front propagation calculator obtains arrival times of the ultrasonic waves for the plurality of the reception focuses on the reception scanning line to obtain wave front propagation time changes for the reception scanning line for each of the plurality of the ultrasonic transducers, and the delay time extractor obtains a delay time curve that indicates a change of the delay time for the reception scanning line based on a distribution of a plurality of the wave front propagation time changes.

3. The ultrasonic imaging apparatus according to claim 2, wherein the delay time extractor extracts a delay time curve that continues from the starting point to the ending point of the reception scanning line as the delay time curve.

4. The ultrasonic imaging apparatus according to claim 2, wherein the reception beamformer comprises a plurality of delay adders that delay the received signals of the plurality of the ultrasonic transducers by the delay times, and then add the delay times to obtain phased signals for one ultrasound probe,
the delay time extractor extracts a plurality of the delay time curves, and
the plurality of the delay adders each obtain phased signal by using delay times of the plurality of the delay time curves.

5. The ultrasonic imaging apparatus according to claim 2, wherein, when two of the delay curves are discontinuous, the delay time extractor connects them to generate a delay time curve that continues from an end to the other end of the reception scanning line.

6. A method for processing ultrasonic signals, comprising:
sending, to a plurality of arranged ultrasonic transducers, ultrasonic signals delayed by a predetermined transmission delay time for each of the plurality of the ultrasonic transducers so that a predetermined transmission beam is formed; and
delaying the ultrasonic signals received by the plurality of the ultrasonic transducers by delay times set for each of the plurality of the ultrasonic transducers after receiving ultrasonic waves transmitted by the ultrasonic transducers for a predetermined reception focus, and then adding them to obtain phased signals,
wherein for each of the plurality of ultrasonic transducers, respective arrival times of ultrasonic waves transmitted from each of the plurality of ultrasonic transducers to the reception focus are calculated based on the predetermined delay time, a distance between the respective transducer and the reception focus and a velocity of the ultrasonic wave,
wherein the delay times are calculated based on a distribution of the calculated arrival times of the ultrasonic waves for each of the plurality of the ultrasonic transducers,
wherein the delay time extractor obtains a synthesized waveform of the ultrasonic waves that arrive at the reception focus from the plurality of the ultrasonic transducers based on distribution of the calculated arrival times of the ultrasonic waves for each of the plurality of the ultrasonic transducers, and calculates the delay times based on a temporal change of amplitude of the synthesized waveform, and wherein the delay time extractor obtains a frequency distribution of the calculated arrival times of the ultrasonic waves obtained by the wave front propagation calculator for each of the plurality of the ultrasonic transducers, and calculates the synthesized waveform by using the obtained frequency distribution.

* * * * *